United States Patent [19]

Royce et al.

[11] Patent Number: 5,556,619
[45] Date of Patent: Sep. 17, 1996

[54] CROSSLINKED POLYMERIC AMMONIUM SALTS

[75] Inventors: Susan D. Royce; Garret D. Figuly, both of Wilmington; Nitya P. Khasat, Newark; Jose R. Matos, New Castle, all of Del.

[73] Assignee: The Du Pont Merck Pharmaceutical Company, Wilmington, Del.

[21] Appl. No.: 202,395

[22] Filed: Feb. 24, 1994

Related U.S. Application Data

[63] Continuation-in-part of Ser. No. 182,954, Jan. 19, 1994, which is a continuation-in-part of PCT/US93/07649, Aug. 18, 1993, which is a continuation-in-part of Ser. No. 932,449, Aug. 20, 1992, abandoned.

[51] Int. Cl.$^6$ ............................................. A61K 31/785
[52] U.S. Cl. ........................... 424/78.08; 424/78.01; 528/422
[58] Field of Search .................. 528/422; 424/78.08, 424/78.1, 78.01

[56] References Cited

U.S. PATENT DOCUMENTS

| | | | |
|---|---|---|---|
| 3,332,841 | 7/1967 | Ainsworth et al. | 167/55 |
| 3,383,281 | 5/1968 | Wolf et al. | 167/65 |
| 3,499,960 | 3/1970 | Macek et al. | 424/33 |
| 3,692,895 | 9/1972 | Nelson et al. | 424/78 |
| 3,778,476 | 12/1973 | Rembaum et al. | 528/422 |
| 3,780,171 | 12/1973 | Irmscher et al. | 424/79 |
| 3,803,237 | 4/1974 | Lednicer et al. | 260/2 |
| 3,974,272 | 8/1976 | Polli et al. | 424/78 |
| 3,980,770 | 9/1976 | Ingelman et al. | 424/79 |
| 4,027,009 | 5/1977 | Grier et al. | 424/78 |
| 4,071,478 | 1/1978 | Shen et al. | 260/2 |
| 4,147,586 | 4/1979 | Petrovich et al. | 162/135 |
| 4,205,064 | 5/1980 | Wagner et al. | 424/78 |
| 4,374,244 | 2/1983 | Green et al. | 542/476 |
| 4,439,419 | 3/1984 | Vecchio | 424/78,79 |
| 4,604,430 | 8/1986 | Johnson | 525/326.7 |
| 4,775,384 | 10/1988 | Bachem et al. | |
| 4,877,775 | 10/1989 | Scopelianos et al. | 514/41 |
| 4,985,410 | 1/1991 | Conti | 514/54 |
| 5,059,685 | 10/1991 | Conti | 536/1.1 |
| 5,091,175 | 2/1992 | Imondi et al. | 424/486 |
| 5,114,709 | 5/1992 | St. Pierre et al. | 424/78.12 |
| 5,236,701 | 8/1993 | St. Pierre et al. | 424/78.12 |

FOREIGN PATENT DOCUMENTS

| | | | |
|---|---|---|---|
| 0081291 | 6/1983 | European Pat. Off. | C08G 73/02 |
| 0373852 | 6/1990 | European Pat. Off. | C08F 8/44 |
| 0375350 | 6/1990 | European Pat. Off. | C08F 8/44 |
| 0387681 | 9/1990 | European Pat. Off. | C08B 37/16 |
| 0385686 | 9/1990 | European Pat. Off. | C08F 8/32 |
| 0400364 | 12/1990 | European Pat. Off. | C08B 37/08 |
| 0403199 | 12/1990 | European Pat. Off. | C08F 8/32 |
| 0403271 | 12/1990 | European Pat. Off. | C08F 8/32 |
| 0403198 | 12/1990 | European Pat. Off. | C08F 8/32 |
| 0402062 | 12/1990 | European Pat. Off. | C08F 8/32 |
| 0400848 | 12/1990 | European Pat. Off. | C08F 8/44 |
| 0432995 | 6/1991 | European Pat. Off. | C08F 220/34 |
| 0459632 | 12/1991 | European Pat. Off. | C08F 20/60 |
| 1249031 | 7/1986 | U.S.S.R. | 528/422 |
| 2036048 | 6/1980 | United Kingdom | C08G 73/00 |
| WO91/18027 | 11/1991 | WIPO | C08F 8/32 |
| WO94/04596 | 3/1994 | WIPO . | |

OTHER PUBLICATIONS

DeSimone, R. et al., *Journal of Pharmaceutical Sciences*, 67, 1965–1698, 1978.

Dick, C. R., et al., *J. Macromal Sci. Chem.*, A4(6), 1301–1314, Oct. 1970.

Stedronsky, E. R., *Biochimica et Biophysica Acta*, 1210, 255–287, 1994.

*Primary Examiner*—Thurman K. Page
*Assistant Examiner*—Peter F. Kulkosky

[57] ABSTRACT

Disclosed are novel crosslinked polymeric ammonium salts wherein in said polymeric salt: about 25% or more of the segments which link ammonium nitrogen atoms are group Y wherein Y is an n-alkylene group or alkyl substituted n-alkylene group, wherein said n-alkylene group has 7 to about 20 carbon atoms; zero to about 75% of segments which link ammonium nitrogen atoms are group Z wherein Z is a hydrocarbylene radical containing 2 or more carbon atoms, said hydrocarbylene radical optionally containing one or more hydroxyl, ether, amino, thioether, keto, or silyl groups or heterocyclic rings; and about 25% or more of the ammonium atoms are secondary ammonium atoms.

36 Claims, No Drawings

CROSSLINKED POLYMERIC AMMONIUM SALTS

CROSS-REFERENCE TO EARLIER FILED APPLICATIONS

This application is a continuation-in-part of U.S. patent application Ser. No. 08/182,954, filed Jan. 19, 1994, which is a continuation-in-part of U.S. patent application Ser. No. PCT/US93/07649, filed Aug. 18, 1993, which is a continuation-in-part of U.S. patent application Ser. No. 07/932,449, filed Aug. 20, 1992 now abandoned. The disclosure of these earlier filed applications is hereby incorporated herein by reference.

FIELD OF INVENTION

This invention concerns novel, crosslinked polymeric ammonium salts and processes for their preparation. Uses for these compositions are as absorbents, adsorbents, electroconductive agents, charge transfer agents, chelating agents and ion exchange resins. These salts are also useful as bile acid sequestrants, i.e., when administered orally, the polymers lower blood cholesterol levels in mammals.

TECHNICAL BACKGROUND

U.S. Pat. No. 4,071,478 describes the use of crosslinked polymers containing quaternary ammonium groups in the polymer backbone which are separated by trimethylene groups. No mention is made of the use of polymers containing ammonium salts which are not quaternary ammonium salts.

U.S. Pat. No. 4,775,384 describes the reaction of various organic compounds containing two halogen groups with various diamines to form polymeric ammonium salts. These salts are described as water soluble, and are thus not crosslinked. After further reactions, they are described as being useful as fiber finishes.

U.S. Pat. No. 4,147,586 describes the reaction of certain dihaloalkanes with alkylene diamines to form "adducts" which are water soluble. The adducts are useful, after reaction with an epihalohydrin, for increasing the wet strength of paper.

Several different types of bile acid sequestrants are known. Some of these are polymers which contain ammonium salts (amine groups in the salt form) which are bound to or are part of a polymer molecule. Such polymers vary in their ability to bind bile acids, their toxicity and their ease of administration. Thus, improved bile acid sequestrants are still being sought.

U.S. Pat. No. 3,383,281 describes the use of crosslinked polymers containing amine groups as bile acid sequestrants. In particular, the use of crosslinked styrenes containing quaternary ammonium groups is described. Such resins, which are also useful as ion exchange resins, are believed to be the active ingredient in the commercially available cholestyramine which is used to lower blood cholesterol levels.

U.S. Pat. No. 4,027,009 describes the use of linear (not crosslinked) polymers containing quaternary ammonium groups in the polymer backbone as bile acid sequestrants. The nitrogen atoms of the polymer are connected by methylene chains of designated size, or other designated groups. No mention is made in this patent of the use of crosslinked polymers (except as background information), or the use of polymers containing ammonium salts that are not quaternary ammonium salts.

U.S. Pat. No. 5,236,701 describes a crosslinked polymeric material useful as a bile acid sequestrant which has amine group on polymer branches which are end groups. The amine groups are not part of the crosslinked network.

R. De Simone, et al., Journal of Pharmaceutical Sciences, vol. 67, p. 1695–1698 (1978) describes the preparation and use of an analog of "Cholestyramine" which is "microporous".

SUMMARY OF THE INVENTION

This invention includes crosslinked polymeric ammonium salts, useful as bile acid sequestrants, as absorbents or as charge transfer agents, said salts comprising ammonium nitrogen atoms linked by segments to other ammonium nitrogen atoms wherein:

about 25% or more of the segments which link ammonium nitrogen atoms are group Y wherein each Y is independently

wherein b is an integer of 7 to about 20, and each $R^1$ and each $R^2$ is independently alkyl, said alkyl preferably having 1 to 20 carbon atoms, more preferably 1 to 10 carbon atoms or hydrogen;

the remainder of the nitrogen atoms are linked by segments Z wherein each z is independently a hydrocarbylene radical containing 2 to 50 carbon atoms, said hydrocarbylene radical optionally containing one or more groups, independently selected from the group consisting of hydroxyl, ether, amino, thioether, keto, or silyl groups and heterocyclic rings;

wherein about 25% or more of the ammonium nitrogen atoms are secondary ammonium nitrogen atoms;

wherein said crosslinked polymeric ammonium salt is insoluble in water; provided that at least some of said ammonium nitrogen atoms are part of a crosslinked network.

This invention includes a method for sequestering bile acids, comprising, contacting in an aqueous medium a bile acid and a crosslinked polymeric ammonium salt, wherein in said salt:

about 25% or more of the groups which link ammonium nitrogen atoms are group Y wherein Y is an n-alkylene group or alkyl substituted n-alkylene group, wherein said n-alkylene group has 7 to about 15 carbon atoms;

zero to about 75% of the groups which link ammonium nitrogen atoms are group Z wherein Z is a hydrocarbylene radical containing 2 or more carbon atoms, preferably 2 to 50 carbon atoms, said hydrocarbylene radical optionally containing one or more groups selected from the group consisting of hydroxyl, ether, ester, amino, thioether, keto, silyl group and heterocyclic rings; and about 25% or more of the ammonium nitrogen atoms are secondary ammonium nitrogen atoms.

In the above defined embodiments, it is preferred if substituents, e.g. hydroxy, ether, amino, thioether, keto or silyl group, on the hydrocarbylene contain 1 to 50 carbon atoms, more preferably 1 to 30 carbon atoms.

It is also preferred if the crosslinked polymeric ammonium salt has a $B_{max}/K_d$ value for cholate of greater than 0.75.

Included in the present invention are pharmaceutically acceptable salts and prodrugs of the above described crosslinked polymeric salts.

This invention also includes preferred methods for the preparation of the crosslinked polymeric ammomium salts of this invention and pharmaceutically acceptable salts thereof.

This invention also also includes improved methods for the preparation of the crosslinked polymeric ammonium salts of this invention having improved bile acid sequestrant properties, wherein said improved methods comprise carrying out the polymerization step for the preparation of the the crosslinked polymeric ammonium salt of the invention in the presence of a template, said template being defined herein below.

The present invention also includes methods for the treatment of hypercholesterolemia and/or lowering blood plasma cholesterol levels in a mammal comprising administering to a mammal a therapeutically effective cholesterol-lowering amount of a crosslinked polymeric ammonium salt as described above.

The present invention also includes pharmaceutical compositions comprising a therapeutically effective amount of a crosslinked polymeric ammonium salt as described above and a pharmaceutically acceptable carrier.

Also included in the present invention are pharmaceutical kits comprising one or more containers containing pharmaceutical dosage units comprising a crosslinked polymeric ammonium salt as described above, for use for the treatment of hypercholesterolemia, for sequestering bile acids, and/or for the lowering of blood cholesterol levels.

The crosslinked polymeric ammonium salt compounds of the present invention can also be administered in combination with one or more additional therapeutic agents. Administration of the crosslinked polymeric ammonium salts of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety. The present invention also includes methods of treating hypercholesterolemia in a mammal by administering a crosslinked polymeric ammonium salt as described above in combination with one or more additional therapeutic agents which may be selected from but not limited to: an inhibitor of acyl-coenzyme A: cholesterol O-acyltransferase (ACAT); an inhibitor of 3-hydroxy-3-methylglutaryl-coenzyme A (HMG-CoA) reductase, such as lovastatin (MEVACOR®); a lipid regulating agents such as gemfibrozil (LOPID®), clofibrate-(ATROMID-S®), or probucol (LORELCO®).

DETAILS OF THE INVENTION

The materials used and described herein are crosslinked polymeric ammonium salts. By crosslinked is meant a polymer which has a network structure. A common test to determine if a polymer is crosslinked is to try to dissolve the polymer in a liquid that is normally a solvent for that polymer. Linear or branched, but not crosslinked, polymers will dissolve in the solvent. Crosslinked polymers do not dissolve, although they may swell to some degree. The polymeric ammonium salts described herein, when not crosslinked, are generally soluble in water or other polar solvents. When crosslinked, the polymeric ammonium salts swell in water, often to form gel-like materials.

For use as a bile acid sequestrant or for lowering blood plasma cholesterol levels the crosslinked polymeric ammonium salts of this invention may be used in dry or nearly dry form or swollen in water. It is preferred if the polymeric ammonium salt used has a swell factor of at least about 4, preferably about 5 to 25 and more preferably about 10 to 20. The swell factor is taken as the ratio of the weight of water imbibed by the polymer divided by the weight of the polymer used. It is believed that the crosslinked polymeric ammonium salts that swell to the preferred levels have certain advantages as blood plasma cholesterol level lowering agents, such as increased capacity to sequester bile acids and soft gel texture which leads to less irritation.

By an ammonium salt or ion is meant a nitrogen atom bonded to four other atoms, for example in the ammonium ion itself, to four hydrogen atoms. In a primary ammonium ion the nitrogen atom is bonded to three hydrogen atoms and one carbon atom, in a secondary ammonium ion it is bonded to two carbon atoms and two hydrogen atoms, in a tertiary ammonium ion to three carbon atoms and one hydrogen atom, and in a quaternary ammonium ion to 4 carbon atoms. In the polymeric ammonium salts of the present invention, at least 25% of the ammonium nitrogen atoms are secondary ammonium nitrogen atoms, preferably at least about 40%. In one preferred embodiment primary ammonium nitrogen atoms are 15 to 25%, secondary ammonium nitrogen atoms are 40–60%, tertiary ammonium nitrogen atoms are 15 to 25% and quaternary ammonium nitrogen atoms are less than 5%, of all of the total ammonium nitrogen atoms in the polymer. Determination of what types of ammonium nitrogen atoms are present is illustrated in Example 53.

Each nitrogen atom of an ammonium salt has one positive charge, and a counterion for the positive charge of each ammonium ion is close by. The counterion may be any negative ion whose conjugate (Bronsted) acid is capable of protonating the conjugate base of the ammonium salt. When used as a cholesterol lowering agent the counterion should be biologically compatible, that does not cause substantial undesired physiological changes. Suitable biologically compatible counterions include chloride, bromide, iodide, sulfate, phosphate, acetate, ascorbate, carbonate, bicarbonate, nicotinate, salicylate, tartrate and citrate. Chloride ion is an especially preferred counterion.

The nitrogen atoms of the ammonium salts (ions) of the polymer are located between polymer segments, unless they are end groups. At least about 25% of these groups, designated herein as Y, linking these nitrogen atoms are independently selected from n-alkylene groups having 7 to about 20 carbon atoms. By an "n-alkylene" group herein is meant the group —$(CH_2)_b$— wherein b is a specified integer, in this instance 7 to about 20. Thus, Y can be represented by the formula —$(CR^1R^2)_b$—, where b is an integer from 7 to 20, and each $R^1$ and $R^2$ is independently alkyl, preferably having 1 to 20 carbon atoms and more preferably having 1 to 10 carbon atoms, or hydrogen. This n-alkylene group Y may also be substituted with alkyl groups, and is then in effect a branched alkylene group. It is preferred if the n-alkylene group has 7 to 14 carbon atoms, and more preferred if it has 9 to 12 carbon atoms. It is contemplated that other hydrocarbylene groups, such as ones wherein the distance between nitrogen atoms is equivalent to at least 7 methylene groups, are also operative.

The other nitrogen atoms of the ammonium salts are connected by hydrocarbylene groups, designated herein as Z, containing 2 or more carbon atoms, preferably 2 to 50 carbon atoms, that is there must be at least two carbon atoms between the nitrogen atoms. By "hydrocarbylene" herein is meant a divalent radical containing only carbon and hydrogen. The hydrocarbylene group Z may be substituted with various substituents or contain in-chain groups containing heteroatoms. It is preferred if the hydrocarbylene group is saturated. Substituents or in-chain groups may include hydroxy, alkoxy, ether, ester, amino, thioether, keto, silyl groups or heterocyclic rings. Preferred substituents are ether and amino groups. It is preferred if the hydrocarbylene group Z is an n-alkylene group containing 2 to 14 carbon atoms. It is also preferred if the substituent contains 1 to 50 carbon atoms, more preferably 1–30 carbon atoms, most preferably 1 to 20 carbon atoms.

Many of the nitrogen atoms located between polymer segments Y and Z (alternatively connected by segments Y and Z), assuming Z is present, are part of the crosslinked network of the polymer. The polymer network may be thought of as a 3 dimensional latticework, with some segments of the lattice not being connected at one end to the lattice. These unconnected segments are usually thought of as polymer ends. What is meant as being "part of the crosslinked network" is that the particular segment or group (which may contain one or more nitrogen atoms) in question is joined at both ends of the segment or group to a crosslinking site (or crosslinking branch point) of the 3 dimensional lattice. Thus, a segment which is connected (eventually) at both ends to the lattice (and any nitrogen atoms it contains) is part of the crosslinked network. It is believed that in these crosslinked polymeric ammonium salts, nitrogen atoms are often the actual crosslinking branch sites, and of course, these nitrogen atoms are part of the crosslinked network.

As used herein, "alkyl" is intended to include both branched and straight-chain saturated aliphatic hydrocarbon groups having the specified number of carbon atoms (the number of carbon atoms may be specified, for example, as "$C_1$–$C_{10}$" to denote alkyl having 1 to 10 carbon atoms). "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", "cycloalkylene" and the like, refer to alkyl, alkenyl, phenyl, and cycloalkyl groups, respectively, which are connected by two bonds to the rest of the structure of the crosslinked polymer of the present invention. Such groups may alternatively and equivalently be denoted as -(alkyl)-, -(alkyenyl)-, -(phenyl)-, -(cycloalkyl)-, and the like, respectively.

As used herein, the term "hydrocarbylene" includes any hydrocarbon group such as, by way of example and without limitation, alkyl, alkenyl, alkynyl, carbocycle, cycloalkyl, alkylcycloalkylalkyl, alkylcarbocycle, or carbocyclealkyl groups, which are connected by two bonds to the rest of the structure of crosslinked polymer of the present invention. By "in-chain" ether, ester, amino, thioether, keto, silyl groups, or heterocyclic rings it is meant that the hydrocarbylene group contains one or more (preferably 1–5 groups, independently selected) in-chain —O—, —OC(=O)—, —C(=O)O—, —NH—, —N($C_1$–$C_{10}$ alkyl)-, —S—, —C(=O)—, —SiH($C_1$–$C_{10}$ alkyl)-, —Si($C_1$–$C_{10}$ alkyl)$_2$, or -(heterocycle)- groups. By "substituent" hydroxy, ether, amino, thioether, keto, silyl groups, or heterocyclic rings it is meant that the hydrocarbolene group is substituted with one or more (preferably 1–5, independently selected) —OH, —O($C_1$–$C_{10}$ alkyl), —($C_1$–$C_{10}$ alkyl)O($C_1$–$C_a$lkyl), —NH$_2$, —NH($C_1$–$C_{10}$ alkyl), —NH($C_1$–$C_{10}$ alkyl)$_2$, —SH, —S($C_1$–$C_{10}$ alkyl), —($C_1$–$C_{10}$ alkyl)S($C_1$–$C_{10}$ alkyl), =O, ($C_1$–$C_{10}$ alkyl), —SiH($C_1$–$C_{10}$ alkyl)$_2$, or -(heterocycle) groups.

As used herein, the term "hydrocarbyl" includes any hydrocarbon group such as, by way of example and without limitation, alkyl, alkenyl, alkynyl, carbocycle, cycloalkyl, alkylcycloalkylalkyl, alkylcarbocycle, or carbocyclealkyl groups, which are connected by one bond to the rest of the structure of crosslinked polymer of the present invention. Such hydrocarbyl group may contain an in-chain or substituent group as described above for a hydrocarbolene group.

"Alkoxy" represents an alkyl group of indicated number of carbon atoms attached through an oxygen bridge; "alkylthio" represents an alkyl group of indicated number of carbon atoms attached through an sulfur bridge; "monoalkylamino" and "dialkylamino" represents a N atom substituted with 1 or 2 alkyl groups, respectively, of the indicated number of carbon atoms; "cycloalkyl" is intended to include saturated ring groups, including mono-, bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heteroaryl" or "heterocyclic ring" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H, 6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quiinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyi, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

The term "substituted", as used herein, means that any one or more hydrogen on the designated atom or group is replaced with a selection from the indicated group, provided that the designated atom's normal valency is not exceeded, and that the substitution results in a stable compound. When a substitent is keto (i.e., =O), then 2 hydrogens on the atom are replaced.

One method of preparing the instant polymeric ammonium salts comprises the reaction of a bifunctional organic compound with a diamine compound said diamine compound having two primary amines. As used herein, the term bifunctional organic compound refers to a compound which may be represented by the formula X—Y—X and/or X—Z—X, where Y and Z are defined above, and X is a suitable leaving group useful for amine alkylation reactions. X may be independently selected from, but not limited to, the following: halides, epoxides, derivatized alcohols, sulfonate esters, aziridines, episulfides, sulfate esters, diazo groups. Other suitable leaving groups for amine alkylation reactions will be recognized by one of skill in the art of organic synthesis. Examples of such suitable leaving groups are found in "Advanced Organic Chemistry" (3rd edtion, J. March. ed., 1985), the disclosure of which is hereby incorporated by reference. Said bifunctional organic compound may also be referred to herein as the "alkylating agent". Y or Z, as defined above, is the group to which the suitable leaving group functionalities are bound.

The diamine compound may be represented by $H_2N$—Y—$NH_2$ and/or $H_2N$—Z—$NH_2$, where Y or Z, as defined above, is the group to which the two amino groups are bound. In order to obtain the desired polymer, at least some of the bifunctional organic compound (for example, dihalide) and/or some of the diamine must contain Y as described above. In order to optimally obtain the desired polymer it has been found that the Y or Z group should be of such a size that the suitable leaving groups (for example, halogen atoms) are the equivalent of about 7 or more methylene groups apart, that is be separated by 7 methylene groups or an equivalent distance if not separated by methylene groups. It is believed that if this minimum separation of the bifunctional organic compound leaving groups is not present, the bifunctional organic compound tends to "back bite" after the first leaving group has reacted with an amine, to give an undesirable cyclic structure. Thus, it is often convenient (but not necessary) that the bifunctional organic compound be X—Y—X. Groups Y and Z may be selected independently at each position in a particular polymer.

Useful bifunctional organic compounds are preferably dihalides and include, but are not limited to, 1,10-dibromodecane, 1,12-dibromododecane, 1,8-dibromooctane, 1,18-dibromooctadecane, 1,9-dibromononane, 1,7-dibromoheptane, 1,8-diiodooctane, 1,8-dibromo-3-ethyloctane, and 1,9-dibromodecane. Useful diamines include, but are not limited to, ethylene diamine, 1,6-diaminohexane, 1,12-diaminododecane, 2-methyl-1,5-diaminopentane, 1,4-bis(aminomethyl)cyclohexane, 1,3-diaminopentane, diethylenetriamine, 1,4-bis(3-aminopropyl)piperazine, 1,4-cyclohexanediamine, 5-amino-1-aminomethyl-1,3,3-trimethylcyclohexane, 1,3-propanediamine, 1,4-butanediamine, 1,5-pentanediamine, 1,7-heptanediamine, 1,8-diaminooctane, 1,9-diaminononane, 1,10-diaminodecane, 1,11-diaminoundecane, 2-hydroxy-1,3-propanediamine, and 4,4'-methylenebis(cyclohexylamine). More than one diamine and/or bifunctional organic compound may be used so long as the limitations imposed on the polymeric structure are met, for example, at least about 25% of the total groups Y and Z should be Y.

The polymeric ammonium salts can also be made by reaction of a diamine with a diepoxide. In this case, it is the diamine in which the nitrogen atoms are connected by an n-alkylene group (which may be alkyl substituted) containing 7 to about 20 carbon atoms. See Examples 57–63 for the preparation of such sequestrants. After synthesis of these polymers, the ammonium salts are formed by neutralization of the amines with acids.

The polyamines (and their salts), as described herein, may have nitrogen atoms that are further substituted, typically by reaction with (substituted) alkyl halides to form for example, secondary amine (salts) from primary amines, and tertiary amines from secondary amines. However, in the resulting polyamine(salt), 25% or more of the amino (ammonium) nitrogen atoms should still be secondary. The group Q which is further substituted on a nitrogen is a hydrocarbyl group containing 1 to 50 carbon atoms, and may contain one or more, preferably 1 to 5, in-chain or substituent hydroxy, ether, amino, thioether, keto, silyl groups or heterocyclic rings. It is preferred if Q contains 1–30 carbon atoms. Such polyamine salts are described in Examples 39 to 50, 69 and 70.

The present invention also includes improved processes for the preparation of the crosslinked polymeric ammonium salts (comprising Y and optionally Z groups, as defined above) of the present invention. The process for the preparation of the crosslinked polymeric ammonium salts of the invention comprises a polymerization step (including gelation) and also preferably comprises one or more of the following steps (which are further described in detail below): a purification step; an ion exchange step; a size reduction; and a drying step. These additional steps may be carried out sequentially in any order or may be carried out concurrently or in combination with one another (i.e., as a single step). The the size reduction step may be carried out after either the polymerization, purification, drying, or ion exchange steps. Additional steps may be added, some steps may be combined and/or done in the same equipment, and/or the order of some steps may be changed in order to improve the overall process. By way of example and without limitation, the purification and ion exchange steps may be carried out concurrently in a single combined step; polymerization and size reduction may be combined; drying and size reduction may be combined; there may be multiple size reduction steps; polymerization, size reduction, purification, and ion exchange may be done in the same equipment; purification, ion exchange, and size reduction may be combined and/or done in the same equipment; and other such combinations and/or exchanges may be done which would improve the overall process. The process and conditions for the preparation of the crosslinked polymeric ammonium salts include, but are not limited to, those processes and conditions described in detail below.

Polymerization

In general, the polymerization step (including gelation) is conducted in such a manner as to allow control of the reactant mole ratio, temperature, time, solvent composition, reagent feed rate, order and mode of reagent addition, monomer concentration, mixing and other reaction variables. The polymeric ammonium salts can be made from the above described diamines and bifunctional organic compounds (for example, dihalides or diepoxides) by dissolving the reactant monomers, either separately or together, in a suitable solvent, typically a polar solvent, such as described below. The reactants are then mixed under controlled conditions using a suitable reactor. Following heating and agitation, the reaction mixture forms a gel or granular crumb-like solid, i.e. undergoes gelation as discussed below. At this point, the crude polymeric ammonium salts are ready for purification, ion exchange, size reduction, and/or drying if so desired.

By "gelation" is meant the point at which the polymer becomes insoluble due to crosslinking. In a suitable solvent, a swollen gel will form at the point at which the polymer becomes insoluable. The gel may become a crumb-like solid upon breaking either by agitation in the reactor or high shear milling, as described below.

The suitable solvent used in the polymerization reaction step may be a single compound or a mixture of compounds. All of the starting materials that react to form the crosslinked polymer should be soluble in the solvent. Useful solvents include polar compounds, such as N,N-dimethylformamide, N,N-dimethylacetamide, dimethylsulfoxide, hexamethyl phosphoramide (HMPA), n-methyl pyrolidone (NMP), isopropanol, methanol, ethanol and other lower alcohols and lower ethers. These may be used in combination with each other or alone. Especially preferred solvents are mixtures of N,N-dimethylformamide and methanol or N,N-dimethylacetamide and methanol.

In the polymerization, the reactant monomer concentrations of the reactant solutions, when taken individually, range from 5% to 60% by weight (wt) relative to the total reaction solution weight. After mixing of the reactant solutions, the overall monomer concentration in the reactor is 5% to 60% by wt where the preferred operating range is 35% to 45% by wt. If the reactants are dissolved together in the solvent, the overall solids loading, or monomer concentration, in the reactor is 5% to 60% by wt where the preferred operating range is 35% to 45% by wt. The monomer concentration in the reaction may effect the crosslink density of the product polymer.

The mole ratio of reactants as well is controlled during the polymerization. Approximately equimolar amounts of the diamine and alkylating agent are reacted. A suitable range for the mole ratio of the diamine compound to bifunctional organic compound is about 0.9–1.4, wherein the preferred range is about 1.0–1.20. The preferred range may be selected to produce a polymer product having the desired crosslink density, as discussed below.

The polymerization may be carried out under a wide range of temperatures, ranging from about −5° C. to the boiling points of the solvents (or lower boiling ingredient). In general, the practical operating temperatures are −5° C.–45° C. during the initial reactant mixing and 60° C.–120° C. following the initial reactant mixing. The preferred ranges are 0° C.–40° C. and 75° C.–85° C., respectively. The cooler initial reactant mixing temperature allows for control (reduction) of quaternary amine formation.

The polymerization step may be carried out in the presence or absence of a suitable base to neutralize the acid by-product of the polymerization reaction if an acid by-product is produced by the polymerization reaction. Suitable bases include, but are not limited to, sodium carbonate or potassium carbonate. Such suitable base is preferably present in an amount of 1–50 mole % relative to the bifunctional organic compound, and preferably in the amount of 10–25 mole %.

The reaction time for the polymerization step may be varied widely according to the diamine and bifunctional organic compound (also referred to herein as an alkylating agent) combination being used. In general, the reaction will take a few minutes to several days before the gelled crosslinked polymeric ammonium salt of the invention is formed. The most typical range is 3–24 hours before gelation occurs with an additional 1–16 hour hold period to ensure completion of reaction.

The polymerization reaction is preferably mixed or agitated during the reaction. The intensity of reaction mixing can be changed during different stages of the reaction. Preferably, the reaction mixture is well stirred prior to the gel point or gelation. Mixing during and after gelation is not critical on the small scale, however, on the large multikilogram reaction scale, mixing during and after the gelation becomes important. Mixing during the polymerization reaction also facilitates product removal by preventing the polymer from forming a single solid mass in the reactor and the gel particle size can be controlled by the judicious selection of the mixing speeds. In general, the faster the mixing during and after gelation, the smaller is the resulting gel particle size of the polymeric ammonium salt present in the reactor.

The rate and order of reactant addition to the reactor may be controlled. In general, the reactants may be added either concurrently or sequentially in any order separately into the reactor. When added sequentially, it is preferred that the rate of addition Of the second reactant to the first reactant in the reactor, be sufficiently fast so as to minimize addition of the second monomer after gelation of the reaction mixture. When the reactant monomers are added consurrently to the reactor, the reactant rate of addition is not critical. The reactants may be added at the same rate (based on equivalents, volumes, and/or weights) where completion of addition for both reactants is simultaneous ("cofeeding"), or the reactants may be added at different rates such that the completion of addition for either reactant continues beyond completion of addition of the other, but preferably prior to gelation.

Suitable reactor equipment for the polymerization reaction will depend on the scale of reaction. Polymerization is preferably carried out in a reactor suitable for mixing the liquid solvents and solid materials while maintaining temperature control of the reactor's ingredients. On the small scale, a conventional flask, optionally with a paddle agitator will suffice. However, on the large scale efficient high shear turbulent bulk mixing is preferred. It is preferred to use a mixer/reactor which is suitable for mixing the polymerization reaction throughout the transition of the reaction from a very low viscosity to a thick solution and then to a gel crumb while maintaining temperature control. Appropriately designed continuous flow reactors such as, by way of example and without limitation, extruders, heat exchangers, in-line mixer and/or a combination of mixer reactors and continuous flow through reactors may also be used.

The crosslink density (as measured by the swell factor in water) of the crosslinked polymeric ammmonium salt of the invention can be controlled by judicious use of solvents, temperature and reaction time during the polymerization step. Other factors affecting crosslink density are monomer mole ratios and concentrations used in the reaction. Some solvents (e.g. $H_2O$, acetonitrile, ethers, EtOH), when used alone, produce polymers that swell very little in water. Mixtures of solvents and solvents such as MeOH can produce highly swellable polymers. Short reaction times and/or lower temperatures produce less crosslinking and a higher degree of swelling.

Crosslinking can also be accomplished by using small amounts of tri- or higher functionality amines, epoxides or halides (see Example 67). Crosslinking can also be accomplished by exposing the uncrosslinked polymeric ammonium salt to ionizing radiation.

In the embodiment mentioned above, when used for bile acid sequestration, the polymeric ammonium salt preferably should have a swell factor of at least about 4 in water. The degree of swellability of the polymer is determined by several major factors. One of these is the degree of salt formation in the polymer, that is what percentage of the amino nitrogen atoms present are in their salt form. The higher this percentage, the more the polymer will swell. It is preferred if at least 80% of the amino groups are in their salt form, and more preferred if at least about 90% are in the salt form. Included within the definition of "polymeric ammonium salt" herein is a polymer where at least about 50% of the amino groups in the polymer are in their salt form. Another factor controlling swellability is the hydrophilicity of the groups between nitrogen atoms. Generally, the more carbon atoms these groups contain, the less hydrophilic they are, and the less the polymer will swell in water. The swell may be affected by the selection of counterion. The final controlling factor is crosslink density. Typically, the higher the crosslink density, the less the polymer will swell.

The conditions during polymer synthesis and handling affect these factors. Thus, swell increases with decreasing monomer concentration in the reaction solution, undergoing a sharp increase at high dilution. The reaction time is also important. The reactants react to form higher molecular weight polymer at longer incubation times. Reaction temperature contributes to MW growth, with elevated reaction temperatures producing higher molecular weight (more crosslinks) in shorter periods of time. The workup procedure also removes low molecular weight polymer and decreases swell. Washing the product with aqueous base, then with acid, shrinks and reswells the polymer, squeezing out soluble components. This effect is exploited during the purification and ion exchange steps below. A further reduction in swell is observed after continuously extracting the polymer with an organic solvent, followed by water, in a Soxhlet apparatus.

The choice of solvent for the polymerization has a large effect on the swellability of the final product. A swell of essentially zero is obtained in media which do not dissolve the reactants. Swell is very low in interfacial systems in which dibromodecane is dissolved in an organic phase and hexamethylenediamine in water. The swell can also be controlled by neutralizing the acid by-product, which is generated, by the addition of bases such as sodium carbonate, potassium carbonate or an organic amine. Other non-nucleophilic bases may also be used. The formation of higher swell polymers is promoted by solvents which dissolve both reactants, especially dipolar, aprotic solvents.

Purification and Counterion Exchange of Product Polymer

In processes for preparing the polymers of the present invention, there is usually some amount of impurities such as solvent, unreacted reactants, some oligomers, and/or polymeric but not crosslinked products. Also present is the polymeric ammonium salt counterion. Also, if a template (as discussed herein below) is included in the polymerization step, such template is removed from the desired product polymeric ammonium salt polymer by such purification step. If it is desired to remove this uncrosslinked (and therefore soluble) fraction, this can be done by extracting the crosslinked (insoluble) polymeric ammonium salt with a suitable solvent for extraction in which the uncrosslinked fraction dissolves, such as water, alcohols, or other solvents suitable for such extraction (the polymeric ammonium salt polymer product is not soluble in this extraction solvent). See for instance Example 1A and 1B. If it is desired, the purification step (removal of impurities) and the ion exchange step (to change of the polymeric ammonium salt counterion) can be carried out and accomplished simultaneously by way of adding a suitable solvent to form a gel, adding a base, such as ammonium hydroxide or NaOH, to form a salt with the original counterion, removing the salt by washing the polymer, and then reacidifying with the conjugate acid of the counterion desired. Procedures of this type are well known in the art. Suitable bases for the extraction purification and ion exchange steps include inorganic bases, such as ammonia, metal hydroxides, metal alkoxides, metal carbonates, and organic bases, such as organic amines. Suitable acids for the extraction purification and ion exchange steps include inorganic acids, such as HCl, and organic acids, such as alkyl and aromatic acids.

The solvents used for the purification and/or ion exchange steps are those in which the materials needed for ion exchange are at least somewhat soluble and preferably those that swell the polymer such as, by way of example and without limitation, the following solvents (or mixtures thereof): water, alcohols, polar protic solvents, polar aprotic solvents, solvents containing the conjugate acid of the desired counterion, solvents containing the desired base for removal of the undesired original couterion, and solvents containing salts of the desired counterions. It is preferred to use water and one or more of the above listed bases or acids for the ion exchange step in the process. It is preferred that the solvents be sufficiently volatile to allow relatively easy removal during drying.

The pH of the product polymer following purification and counterion exchange should preferably be in the range of about pH 2–8 and more preferably pH 3–7.

Methods used for the separation of solids and liquids in the extraction purification of the polymeric ammonium salt product include, but are not limited to, Soxhlet extraction, filtration, centrifugation, and/or other such methods used for the separation of solids and liquids. Counter-current extraction methods may be used in the purification step. In applying such methods for the physical separation of solids and liquids, a wide variety of equipment may be employed. These include but are not limited to metal or polymer based screens, cloths, fritted or scintered glass or metal, depth filtration medium, and/or membranes. The optimal means for separation will vary according to the specific polymeric ammonium salt, the solvent and/or solvent mixture being employed, and the state of ionization of the polymer.

Gel Particle Size Reduction of Product Polymer

Size reduction (also referred to herein as milling) of the polymeric ammonium salt gel particles obtained after or during either polymerization, purification, ion exchange and/or drying may be accomplished by several means.

As discussed above, gel particle size reduction of the product polymer is typically and preferably accomplished during the polymerization step by mixing or agitation of the reaction in the reactor.

The particle size reduction may be done in either the wet, damp, frozen or dry state of the crosslinked polymeric ammonium salt product. Mill types useful for particle size reduction include, but are not limited to, a pin mill, hammer mill, cutting mill, rotor-stator mill, media mill, attritor, jet mill, air classifying mill, opposing air jet mill, and/or sonicator. The milling may be done on either a batch, semibatch, or continuous flow through basis, the preference of either being dictated by the location of the mill step in the process, the state of the polymeric ammonium salt, the solvent content of the polymer, the degree to which the polymer is swollen, and the improvement of overall process efficiency. Depending on the specific step within the process after which the size reduction step is done, the judicious selection and use of the appropriate mill method will produce the desired particle size range polymeric ammonium salt particles.

When size reduction is done in the wet state, the solvent used for slurrying the polymer may be either a swelling or nonswelling solvent depending on the type of milling under consideration. When size reduction is done in the damp or dry state it is possible for a combination drying-milling or purification-milling operation to be done. When size reduction is done in the dry state, the polymer may be milled at several temperature ranges: cryogenic, such as liquid nitrogen or carbon dioxide; ambient; and elevated, up to ~150° C. (below temperatures which may cause significant degradation of the polymer).

Drying of Product Polymer

The polymeric ammonium salt product of the present invention is preferably dried so as to remove solvent. By drying is meant the removal of solvent from the polymer matrix. Methods commonly used by those skilled in the art of drying may be employed. Methods for drying include, but are not limited to, tray drying, spray drying, flash drying, rotary paddle drying (either vertical or horizontal, and/or agitated drying, wherein the polymer is exposed to heat, vacuum, and/or dry gas convection to effect the removal of solvent.

When polymeric ammonium salts are wetted with higher boiling solvents, drying time is longer than when they are wetted with lower boiling solvents, and it may be desirable to perform a solvent displacement. For example, a polymeric ammonium salt wetted with water will take approximately five fold longer to dry than the same polymer wetted with methanol when the same drying method is employed. The solvent displacement may be accomplished by several means which include, but are not limited to, azeotropic distillation, direct displacement, or salting out.

In azeotropic distillation, the polymeric ammonium salt wetted with the undesired solvent is heated in the desired solvent and an azeotropic distillation performed. Azeotropic distillation will only work, if the two solvents under consideration form an azeotrope. For example, a water wetted polymeric ammonium salt may be azeotropically distilled in toluene to effect removal of the water.

In direct displacement, the polymeric ammonium salt wetted with the undesired solvent is placed in an apparatus which allows for the physical separation of solids and liquids, as described above. The second solvent is added to the already wetted polymer and after a suitable equilibration time, the solvents are removed. Repeated exposure of the wetted polymer to the desired solvent will eventually effect a displacement of the undesired solvent. For example, water wetted polymeric ammonium salts, placed in a filtration apparatus, would be treated with alcohol and allowed to equilibrate. Following filtration, the mother liquor would now contain both the desired and undesired solvent. Repeated treatment, with alcohol, of the polymer in the filtration equipment will ultimately effect displacement of the water by the alcohol.

In salting out, a polymeric ammonium salt wetted with water, or other salt dissolving solvent, is treated with an inorganic salt, either solid or dissolved in a solution, to effect a collapse of the polymer matrix with concomitant desolvation, i.e., the change in solvent dielectric constant, by the addition of salt, causes the polymer to collapse and squeeze out the undesired polymer. The degree to which the polymeric ammonium salt matrix collapses may be related to the concentration of salt in solution. Salts that may be used for salting out include, but are not limited to, metal halides, metal carbonates, metal phosphates, metal sulfates, and metal carboxylates. For example, when a water wetted polymeric ammonium salt is treated with NaCl, either solid or in solution, the polymer matrix collapses and initially polymer bound water may then be readily filtered off.

Depending on the polymeric ammonium salt being produced, the appropriate method for drying is chosen. The judicious use of either of these described drying methods will result in the preparation of polymeric ammonium salts containing the desired amount of solvent.

During the drying operation, it may be desirable to control final gel particle size. This may be accomplished by performing the drying operation in a piece of equipment equipped with appropriate high shear agitation.

Templating

The in vivo efficacy of polymeric crosslinked bile acid sequestrants may be improved by carrying out the gelation of the polymer (during the polymerization step described above) in the presence of a "sequestrant enhancer", also referred to as "template" herein. The terms "template", "template material", "templating agent" or "sequestrant enhancer", as used herein, means a chemical substance which is substantially inert to the reaction, reaction starting materials and products, and that effects an enhancement of the bile acid sequestering property of the polymer product.

The present invention includes improved methods for the preparation of the crosslinked polymeric ammonium salt polymer (comprising Y and Z groups, as defined above) of the present invention, wherein the improvement comprises carrying out the polymerization and/or gelation step for the synthesis of such crosslinked polymeric ammonium salt polymer in the presence of a template, thereby to enhance the bile acid sequestrant properties of such crosslinked polymeric ammonium salt polymer.

Templates, as described herein, may be used in the polymerization and/or gelation process for the synthesis of other bile acid sequestrant polymers, other than the crosslinked polymeric ammonium salts of the present invention comprising Y and Z groups as described above. Thus, the present invention also includes improved methods for the preparation of other bile acid sequestrant polymers, wherein the improvement comprises carrying out the polymerization and/or gelation step for the synthesis of such other bile acid sequestrant polymer in the presence of a template, thereby to enhance the bile acid sequestrant properties of such other bile acid sequestrant polymer. Such "other bile acid sequestrant polymer" includes, but is not limited to, colestipol hydrochloride and cholestyramine.

Scanning electron micrographs of the crosslinked polymers of the invention prepared in the presence of the templates generally show a porous or reticulated structure with pore size ranging from about 1 to 300 microns depending on the overall particle size of the crosslinked polymer. This is in contrast to the appearance of the same crosslinked polymeric materials prepared in the absence of templates which exhibit essentially no porous structures.

For convenience, and it is preferred, the templates should be added at the beginning of the crosslinking and/or polymerization reaction. Normally, the template will remain in the gel until it is removed, as by solvent extraction (as discussed above and further below).

The process for the synthesis of the uncrosslinked polymers of the invention is carried out in solution (until gelation occurs, at which time the bile acid sequestrant being formed becomes crosslinked and insoluble), in the sense that the starting materials which react to form the crosslinked polymer are in solution. If a template is used, it may be soluble, partially soluble, or insoluble in the reaction medium (the solvent and starting materials for the crosslinked polymer).

The template should be soluble in a solvent (not necessarily the solvent used in the crosslinking process) so that it can be separated from the crosslinked polymeric bile acid sequestrant which is produced in the instant process. This separation would occur during the purification step of the present invention. For instance, the template may be separated from the crosslinked polymer by extraction of the crosslinked polymer with a solvent in which the template is soluble. This can be the same solvent as used in the instant process if a soluble polymer is used as the template. Solvent extraction also encompasses use of a solvent as the extractant which chemically converts the enhancer to a soluble material, while not substantially affecting the polymer structure of the crosslinked polymer. For example, an aqueous acid, such as aqueous HCl, may be used to convert the template to a soluble material. HCl may also convert the polymeric ammonium salt to a chloride. Thus, the solvent used to remove the template from the crosslinked polymer of the invention may change the salt form of the crosslinked polymer. After extraction of the template, the crosslinked polymeric bile acid sequestrant may, if desired, be isolated in pure form by removal of the extraction solvent, as by filtration and/or evaporation in air or under vacuum.

Templates which are insoluble in the reaction medium may, preferably, have a particle size of less than about 1000 microns (measured as being able to pass through a sieve of that size), more preferably less than about 600 microns. Such particle sizes may be made, for example by grinding a solid substance, or by dispersing a liquid substance (including a polymer) in the solvent beforehand using high shear. Dispersion of the insoluble template during the process can be maintained by simple means, such as agitation.

The template should not interfere in the reaction(s), as described earlier, which form the crosslinked polymer of the invention, and should not, itself, become part of the chemical structure of the crosslinked polymer. The enhancer should also not strongly coordinate with any of the starting materials for the crosslinked polymeric bile acid sequestrant, or the crosslinked polymer itself.

Polymers for use as templates include both natural and synthetic polymers, including both thermoplastics and elastomers. Useful polymers include, but are not limited, to polyacrylates, polymethacrylates, polyvinylpyrrolidone, poly(vinyl acetate), various starches, corn products such as amaizo, amylose and zein, pectin, alkoxylated celluloses, polyesters and polyethers.

Representative organic polymeric template substances also include cellulose polymers (such as ethylcellulose, hydroxypropylcellulose, methylcellulose, and hydroxypropylmethylcellulose), polyethylene glycol, proteins, nucleic acids, albumin, gelatin, starch, collagen, dextran and modified dextrans, polysaccharides, polylactide/polyglycolide, polyalkylcyanoacrylates, polyacrylamide, polysorbates, polyethylene ethers and esters, and polyoxyethylene/polyoxypropylene block polymers.

Suitable templates may also include natural and synthetic gums (such as acacia, tragacanth, or sodium alginate), sodium oleate, sodium stearate, magnesium stearate, sodium benzoate, sodium acetate, agar, bentonite, xanthan gum, phospholipids (such as cholesterol, stearylamine, or phosphatidylcholines), and soluble polymers such as polyvinylpyrrolidone, pyran copolymer, polyhydroxypropylmethacrylamide-phenol, polyhydroxyethylaspartamidephenol, or polyethyleneoxide-polylysine substituted with palmitoyl residues. Other polymers useful as templates may include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Preferred polymers include poly(2-hyroxyethyl methacrylate), polyvinylpyrrolidone, poly(vinyl acetate), potato starch, wheat starch, pea starch, gellan gum, welan gum, rhamsam gum, xanthan gum, amaizo, amylose, zein, pectin, hydroxypropyl cellulose, carboxymethylcellulose, polyester glycols and polyether glycols. Nonpolymeric templates include, but are not limited to: mono- or disaccharides, such as galactose, lactose, trehalose, and sucrose; steroid derivatives, cholesterol derivatives, bile acid derivatives, such as cholesterol esters, sodium cholate, methyl cholate, and cholesteryl chloride; and inorganic materials and salts, such as metal halides (for example, KCl and NaCl), metal carbonates, borates and phosphates (and salts thereof). Also useful as templates are metal carboxylates, such as acetates, propanates, butyrates, salicylates, gluconates, ascorbates, citrates, and salts thereof. Inorganic material useful as a template in the present invention includes boraxes and phosphates (and salts thereof) in the form of monomeric salts or as polymeric forms, or as mixtures of monomeric and polymeric forms. The inorganic material may be in a crystalline and amorphous form, or a mixture of crystalline and amorphous forms. Preferred lower molecular weight templates are trehalose, sodium chloride, methyl cholate and cholesteryl chloride.

One or more of the above-described templates may be used in combination in a particular polymerization and/or gelation step for the synthesis of the crosslinked polymers of the present invention.

The proportions of the various reaction ingredients (reactant starting materials, template, solvent) for the polymerization/gelation in the presence of template may be selected as described above for the polymeriziation step (as in the absence of template). The stoichiometry of the materials (i.e., monomers and/or polymers) which will form the crosslinked polymer may be important to obtaining the preferred desired crosslinked polymer, as it is in the absence of template, as described above. Useful proportion ranges of the template are 5 to 500 percent by weight (of the entire reaction mass) of template, 5 to 500 percent by weight of solvent and 5 to 500 percent by weight of the materials which will form the crosslinked polymer.

The improved polymeric ammonium salts with enhanced bile acid binding properties which are prepared using a template, may be further processed as described above by purification, ion exchange, size reduction, and/or drying.

The polymeric ammonium salts of the present invention are useful as bile acid sequestrants (which lower blood plasma cholesterol levels), moisture or solvent absorbents, electroconductive agents, charge transfer agents, chelating agents and ion exchange resins.

Preferred compositions herein of the polymeric ammonium salts which are useful as bile acid sequestrants have a $B_{max}/K_d$ value for cholate of greater than 0.75, more preferably 1.0 or more. $B_{max}$ is the maximum amount of bile acid (in this case cholate) bound per unit of crosslinked polymer of the invention, wherein Bmax is expressed in units of μmol of bile acid (in this case cholate) bound per mg of dry crosslinked polymer of the invention. $K_d$ (or Kd) is the concentration of free bile acid (in this case cholate) at which there is half-maximal binding of the bile acid to the crosslinked polymer of the invention. Kd is expressed in units of mM. The binding of bile acid to the crosslinked polymer of the invention may be measured using the procedures described herein below. The $B_{max}$ and Kd values are determined by best-fit regression fitting the binding data using either Equation 1 or Equation 2, below:

$$[Bound]=(B_{max} \times [Free]^n)/((Kd)^n+[Free]^n) \quad \text{Equation 1}$$

where [Bound] and [Free] are the concentration of polymer-bound and free bile acid (in this case cholate), respectively, and n is a curve fitting parameter.

The ligand-ligand interaction model isotherm that is used is represented by Equation 2:

$$B=(B_{max}/2)\{1+((F/Kd)-1)/Sqrt[((F/Kd)-1)^2+4F/W \times Kd)]\} \quad \text{Equation 2}$$

where F is the free bile acid concentration; W is the ligand ligand interaction parameter or cooperativity parameter; and Sqrt is the square root of the quantity in brackets. (See McGhee and Von Hippel, J. Mol. Biol., 86: 469–489 (1974); Chemistry, Part III, C. Cantor and P. Schimmel (1980), pages 878–885 and pages 1242–1251.)

As noted above, a utility for the crosslinked polymeric ammonium salts of the present invention is as bile acid sequestrants for lowering blood plasma cholesterol in mammals. Coronary and peripheral vascular diseases are major problems in Western society and elevated blood cholesterol levels is one of the major risk factors in the development of atheroscherosis in animals as well as in humans. Several studies using lipid-lowering agents have shown the beneficial effects of lowering cholesterol and low-density lipoprotein (LDL) cholesterol in the prevention of coronary heart disease.

The only quantitatively significant way by which the body can eliminate cholesterol is via the bile, either by excretion of the sterol in unchanged form or after its conversion into bile acids. Cholesterol is catabolized in the liver to bile acids which are transported to the intestine through the bile ducts to facilitate the uptake of dietary lipids.

About 95% of bile acids secreted to the gut are reabsorbed. A small amount of bile acids are lost and excreted with feces. The losses are compensated for by new synthesis. In animals and in man, treatment with bile acid binding resins such as cholestyramine, which bind bile acids in the intestine and prevent their reabsorption, increases fecal bile acid excretion. The increased fecal loss of bile acids is balanced by stimulation of bile acid synthesis from cholesterol in the liver, and there is a resulting decrease in plasma cholesterol levels. It has been shown that plasma cholesterol lowering after bile acid sequestrant treatment is due to increased hepatic cholesterol uptake via enhanced LDL receptor activity.

As described in the Examples below, the crosslinked polymeric ammonium salts of the present invention efficiently bind bile acids and are effective in lowering plasma cholesterol levels when administered to animals.

Also included in the present invention are pharmaceutically acceptable salts and prodrugs of the above-described crosslinked polymeric ammonium salts. As used herein, "prodrugs" refer to derivatives of the disclosed compounds made by modifying functional groups present in the compounds in such a way that the modifications are cleaved, either in routine manipulation or in vivo, to the parent compounds. Examples pf prodrug derivatives include, but are not limited to acetate, formate and benzoate derivatives and the like.

"Pharmaceutically acceptable salts" of the compounds of the invention can be prepared by reacting the free base forms of these compounds with a stoichiometric amount of the appropriate acid in water or in an organic solvent, or in a mixture of the two. Lists of suitable salts are found in *Remington's Pharmaceutical Sciences.*, 17th ed., Mack Publishing Company, Easton, Pa., 1985, p. 1418, the disclosure of which is hereby incorporated by reference.

DOSAGE AND FORMULATION

The bile acid sequestrant polymers of the invention can be administered as cholesterol lowering agents by any means that produces contact of the active agent with bile acids in the gut of a mammal. The bile acid sequestrant polymers of the invention are preferably administered orally, and are administered either as individual therapeutic agents or in combination with other therapeutic agents, such as with other hypocholesterolemic agents and other drugs for the treatment of cardiovascular diseases. They can be administered alone, but generally administered with a pharmaceutical carrier selected on the basis standard pharmaceutical practice.

By "administered in combination" or "combination therapy" it is meant that the crosslinked polymeric ammonium salt compound and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

By "therapeutically effective amount" it is meant an amount of a crosslinked polymeric ammonium salt of the invention that when administered to a mammal binds with bile acids in the intestinal tract of the mammal thereby to increase fecal loss of bile acids and preventing the absorption of the bile acids. The crosslinked polymeric ammonium salts of the invention when administered alone or in combination with an additional therapeutic agent to a mammal are effective to reduce blood serum cholesterol levels to prevent or ameliorate a hypercholesterolemia disease condition or the progression of the disease.

The dosage administered will, of course, vary depending upon known factors, such as the pharmaco-dynamic characteristics of the particular agent and its mode and route of administration; the age, health and weight of the recipient; the nature and extent of the symptoms; the kind of concurrent treatment; the frequency of treatment; and the effect desired. By way of general guidance, the daily dosage of active ingredient may be, for example, an oral dose of about 0.1 to 10 grams being administered 1–4 times a day. The bile acid sequestrant polymers of the invention may be administered for a period of continuous therapy of one month or more, sufficient to achieve the required lowering in serum cholesterol levels.

Dosage forms (compositions suitable for administration) contain from about 0.1 gram to about 10 grams of active ingredient per unit. In these pharmaceutical compositions the active ingredient will ordinarily be present in an amount of about 20–95% by weight based on the total weight of the composition.

The active ingredient can be administered orally in solid dosage forms, such as capsules, tablets, and powders, or in liquid dosage forms, such as elixirs, syrups, and suspensions. Formulation of dosage forms of the polymers of the present invention must take into account the swelling of the particular polymers by water or other solvents.

The polymers of the invention can also be incorporated in a variety of edible solid or liquid forms or in foods such as bars, bread, cookies, cake, cereals, desserts, and the like.

The polymers of the invention may be administered in tablet or in gelatin capsules containing solid bile acid sequestrant polymer or an aqueous or semi-aqueous suspension of solid polymer containing a suitable suspending agent. Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers. Antioxidizing agents such as sodium bisulfite, sodium sulfite, or ascorbic acid, either alone or combined, are suitable stabilizing agents. Also used are citric acid and its salts and sodium EDTA. In addition, solutions can contain preservatives, such as benzalkonium chloride, methyl- or propyl-paraben, and chlorobutanol.

The pharmaceutical compositions of the present invention can be prepared by techniques known to those skilled in the art of pharmacy. Suitable pharmaceutical carriers and formulations are described in *Remington's Pharmaceutical Sciences*, Mack Publishing Company, a standard reference text in this field.

Useful pharmaceutical dosage forms for administration of the polymers of this invention can be illustrated as follows:

Capsules

A large number of unit capsules are prepared by filling standard two-piece hard gelatin capsules each with 0.5 gram of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 0.5 gram of the active ingredient. The capsules are washed and dried.

Tablets

A large number of tablets are prepared by conventional procedures so that the dosage unit is 0.5 gram of active ingredient, 0.2 milligrams of colloidal silicon dioxide, 0.5 gram of magnesium stearate, 275 milligrams of microcrystalline cellulose, 11 milligrams of starch and 98.8 milligrams of lactose. Appropriate coatings may be applied to increase palatability or delay absorption.

Suspension: An aqueous suspension is prepared for oral administration so that each dose contains 500 milligrams of finely divided gelled active ingredient, 200 milligrams of sodium carboxymethyl cellulose, 5 milligrams of sodium benzoate, 1.0 grams of sorbitol solution, U.S.P., and 0.025 milliliters of vanillin.

The crosslinked polymeric ammonium salt compounds of the present invention may be administered in combination with one or more additional or second therapeutic agents which may be selected from, but not limited to: an inhibitor of a acyl-coenzyme A: cholesterol O-acyltransferase (ACAT); an inhibitor of 3-hydroxy-3-methylglutaryl-coenzyme A (HMG-CoA) reductase, such as lovastatin; a lipid regulating agent, such as gemfibrozil, clofibrate, or probucol. The crosslinked polymeric ammonium salt compound of the present invention and such additional therapeutic agent can be administered separately or as a physical combination in a single oral dosage unit. The crosslinked polymeric ammonium salt compound of the present invention may be formulated together with the second therapeutic agent in a single dosage unit (that is, combined together in one capsule, tablet, powder, or liquid, etc.). When the crosslinked polymeric ammonium salt compound of the present invention and the second therapeutic agent are not formulated together in a single dosage unit, the crosslinked polymeric ammonium salt compound and the second therapeutic agent man be administered essentially at the same time, or sequentially in any order.

The dosage of the crosslinked polymeric ammonium salt compound when administered alone or in combination with a second therapeutic agent may vary depending upon various factors such as the pharmacodynamic characteristics of the particular agent and its mode of administration, the age, health and weight of the recipient, the nature and extent of the symptoms, the kind of concurrent treatment, the frequency of treatment, and the effect desired, as described above. The proper dosage of the crosslinked polymeric ammonium salt compound when administered in combination with the second therapeutic agent will be readily ascertainable by a medical practitioner skilled in the art, once armed with the present disclosure. When one or more second therapeutic agents are administered with the crosslinked polymeric ammonium salt compound, generally the amount of each component in a typical daily dosage and typical dosage form may be reduced relative to the usual dosage of the agent when administered alone, in view of the additive or synergistic effect of the therapeutic agents when administered in combination.

The present invention also includes pharmaceutical kits useful for the treatment of hypercholesterolemia, which comprise one or more containers containing pharmaceutical dosage units comprising a pharmaceutical composition comprising a therapeutically effective amount of a crosslinked polymeric ammonium salt compound of the present invention. Instructions, either as inserts or as labels, indicating quantities of the dosage units to be administered, guidelines for administration the dosage units, etc., may also be included in the kit.

In the present disclosure it should be understood that the specified materials and conditions are important in practicing the invention but that unspecified materials and conditions are not excluded so long as they do not prevent the benefits of the invention from being realized.

In the following examples, MeOH is methanol, EtOH is ethanol, DMAC is N,N-dimethylacetamide, DMF is N,N- dimethylformamide, DBD is 1,10-dibromodecane, and HMD is 1,6-hexamethylenediamine.

DETERMINATION OF POLYMER SWELL FACTOR

Into a pre-dried, tared,; 150 mL coarse fritted filter funnel is added about 1 g of polymer. The stem of the funnel is sealed with a rubber stopper. The funnel is placed on a filter flask and about 100 mL of distilled water at about 25° C. is added to the funnel. The contents are stirred, if necessary, to fully disperse the water and polymer. The contents are then left undisturbed for 15 minutes. The rubber stopper is then removed from the stem of the funnel, suction is applied to the funnel for 5 minutes. The stem and underside of the funnel are then rinsed with ethanol to remove any remaining water droplets and suction is then continued for an additional 5 minutes. Any remaining water droplets are wiped of the funnel with a paper towel. The funnel and contents are then weighed to determine the weight of water retained by the polymer.

Swell Factor = (Total wt. of wet polymer + funnel) − (Total wt. of dry polymer + funnel)/ wt. of dry polymer.
= wet wt. − dry wt./dry wt.
= g water retained/g polymer

EXAMPLE 1A

The following procedure illustrates one of the small scale methods used for the preparation of the polymers of the present invention. Into a 1 L three-necked flask equipped with a heating mantle, reflux condensor, overhead stirrer, and nitrogen inlet was added 130 ml of DMF, 130 ml of MeOH, 46.4 g (0.40 mole) of hexamethylene diamine, and 120.0 g (0.40 mole) of 1,10-dibromodecane. The resulting homogeneous solution was stirred rapidly and hearted to reflux. After 0.5–3 hours of reflux the entire contents of the flask became a swollen gelled mass. The stirring was stopped and the flask was gently healed for an additional 18–21 hours. After heating, the gel was allowed to cool to room temperature and was scooped out of the reaction vessel. The gel was then put into a Waring Blender with an equal volume of tetrahydrofuran (THF) and was ground in the blender. This procedure was repeated at least 3 times with filtration between each chopping. The resulting washed polymer was then put into a vacuum oven set at 50°–120° C. for a period of 1–3 days to affect drying. Dry weight was 160 g (96%). To ensure purity, the polymer was then Soxhlet extracted with methanol for 3.5 days and with water for an additional 3.5 days. During this process approximately 30% of the mass of the product was extracted into the solvents. The resulting polymer is dried under vacuum to afford a granular cream colored product. The polymer had a faint "nutty" odor.

The bromide counterion or any other counterion, can readily be exchanged by exposing swollen wet ($H_2O$) polymer to a 10% solution of ammonium hydroxide. The neutralized polymer shrinks (deswells) and is filtered and washed with water until the resulting filtrate is neutral to pH paper. The polymer is then reacidified with the appropriate acid to give the desired counter ion (e.g., HCl for Cl-ion; HOAc for acetate ion; etc.). Upon reacidification, the polymer swells again. The swollen polymer is then washed with water until the filtrate is neutral to pH paper and dried under vacuum to yield a granular polymer With a different counter ion.

Examples 2–38, Table 1, were carried out in a similar manner to Example 1A. Reflux and heating times were the same as in Example 1A.

EXAMPLE 1B

SMALL SCALE PREPARATION OF TEMPLATED POLYMERIC AMMONIUM SALT IN A HIGH SHEAR BENCHTOP REACTOR

A solution of 180 g methanol and 212 g of DMAC was prepared. 149.5 g of DBD was dissolved in 85 g of the solvent mixture. Ten mL of the solvent mixture was reserved for a feed rinse.

The remaining solvent mixture was charged to a 1 quart planetary mixer followed by 52.5 g of hydroxypropylcellulose (HPC) (85,000 MW). The speed of the agitator was set to 90 rpm. The material was heated to 60° C. for one hour with an external circulating heater to dissolve the HPC. The solution was cooled to 40° C. and 54 g of hexamethylene diamine and 26.8 g of sodium carbonate added.

The solution of DBD in the solvent mixture was added over a period of 30 minutes at a constant rate using a piston pump, maintaining the temperature at 40° C., followed by the ten mL of solvent mixture saved for a rinse.

The temperature of the reaction mixture was raised by 10° C. every 15 min until the temperature was 80° C.

The viscosity of the solution increased and after 3 hours the agitator speed was reduced to 7 rpm. The polymerization was continued for an additional 16 hours at 80° C.

The polymer gel (crumb-like solid) was cooled to 25° C. and 2000 mL water and 65.8 g of 50% NaOH were charged to give a final pH of 12.2. After agitating for one hour the slurry was divided into three equal parts. An additional 500 mL was added to one third of the slurry and filtered using vacuum. The cake was washed with 400 mL water.

The cake was slurried in 1000 mL water and sufficient 35% HCl added to adjust the pH to less than 2.5. The slurry was agitated for one hour and filtered. The purification cycle (adjust to pH >12., filter, wash, adjust to pH <2.5, filter) was repeated four times. The last pH of the last acidification was <1.5. The cake was washed 3 times with 900 mL water to a final pH of 4.8.

The wet cake was dried in a small glass rotary dryer to yield 118.5 g or 74% theoretical yield based on the weight of the monomers charged. The swell of the dried polymer was 16.

TABLE 1

Preparation of Polyamine Salts

| Example | Ingredients (wt. g) | Solvent (vol. ratio) | Total Solvent (mL) | Temperature °C. | Final Counterion | Polymer Yield (g) |
|---|---|---|---|---|---|---|
| 2 | 1,4-bis(3-aminopropyl)piperazine (80.0)<br>1,10-dibromodecane (120.0) | DMF-MeOH (1:1) | 260 | reflux | Br | 91.9[a] |
| 3 | hexamethylenediamine (46.4)<br>1,10-dibromodecane (120.0) | MeOH | 260 | reflux | Br | 164.2[b] |
| 4 | 1,12-diaminodecane (30.0)<br>1,12-dibromodecane (49.2) | DMF-MeOH (1:1) | 120 | reflux | Br | 52.5[a] |
| 5 | hexamethylenediamine (45.4)<br>1,10-dibromodecane (120.0) | water | 260 | reflux | Br | 108.3[b] |
| 6 | 1,4-cyclohexane bis(methylamine) (28.4)<br>1,10-dibromodecane (60.0) | DMF-MeOH (1:1) | 150 | reflux | Br | 86.6[b] |
| 7 | 4,4'-methylenebis(cyclohexylamine) (42.0)<br>1,10-dibromodecane (60.0) | DMF-MeOH (1:1) | 150 | reflux | Br | 97.5[b] |
| 8 | 2-methyl-1,5-pentanediamine (23.2)<br>1,10-dibromodecane (60.0) | DMF-MeOH (1:1) | 140 | reflux | Br | 73.2[b] |
| 9 | cis and trans-1,4-diaminocyclohexane (22.8)<br>1,10-dibromodecane (60.0) | DMF-MeOH (1:1) | 140 | reflux | Br | 75.9[b] |
| 10 | hexamethylenediamine (46.4)<br>1,10-dibromodecane (120.0) | DMF-MeOH (1:1) | 260 | RT | Br | 152.5[b] |
| 11 | ethylenediamine (12.0)<br>1,10-dibromodecane (60.0) | DMF-MeOH (1:1) | 140 | reflux | Br | 40.5[b] |
| 12 | metheneamine (14.0)<br>1,10-dibromodecane (30.0) | DMF-MeOH (1:1) | 70 | RT | Br | 24.4[b] |
| 13 | t-1,4-cyclohexanediamine (22.8)<br>1,10-dibromodecane (60.0) | DMF-MeOH (1:1) | 140 | reflux | Br | 59.7[b] |
| 14 | isophoronediamine (17.0)<br>1,1-dibromodecane (30.0) | DMF-MeOH (1:1) | 70 | reflux | Br | 35.0[b] |
| 15 | 3,3-diamino-1,2,4-triazole (9.9)<br>1,10-dibromodecane (30.0) | DMF-MeOH (1:1) | 70 | reflux | Br | 18.8[a,c] |
| 16 | 1,3-diaminopentane (10.2)<br>1,10-dibromodecane (30.0) | DMF-MeOH (1:1) | 70 | reflux | Br | 41.0[b,c] |
| 17 | hexamethylenediamine (5.8)<br>2-methyl-1,5-pentanediamine (5.8)<br>1,10-dibromodecane (30.0) | DMF-MeOH (1:1) | 70 | reflux | Br | 40.0[b] |
| 18 | diethylenetriamine (10.3)<br>1,10-dibromodecane (30.0) | DMF-MeOH (1:1) | 70 | reflux | Br | 25.2[a] |
| 19 | 2-methyl-1,5-pentanediamine (11.6)<br>1,10-dibromodecane (30.0) | DMF-MeOH (1:1) | 70 | RT | Br | 37.3[b] |
| 20 | t-1,4-diaminocyclohexane (5.7)<br>hexamethylenediamine (5.8)<br>1,10-dibromodecane (30.0) | DMF-MeOH (1:1) | 70 | reflux | Br | 40.2[b] |
| 21 | cis- and trans-1,4-diaminocyclohexane (5.7)<br>hexamethylenediamine (5.8)<br>1,10-dibromodecane (30.0) | DMF-MeOH (1:1) | 70 | reflux | Br | 37.9[b] |
| 22 | t-1,4-diaminocyclohexane (5.7)<br>isophoronediamine (8.5)<br>1,10-dibromodecane (30.0) | DMF-MeOH (1:1) | 70 | reflux | Br | 40.7[b] |
| 23 | dimer diamine (30.0)[d]<br>1,10-dibromodecane (15.0) | DMF-MeOH (1:1) | 80 | reflux | Br | 36.3[b] |
| 24 | hexamethylenediamine (278.4)<br>1,10-dibromodecane (720) | DMF-MeOH (1:1) | 1560 | reflux | Br | 993.7[b] |
| 25[e] | polymer of Example 1 (10.0) | | | | Cl | 5.59 |
| 26[e] | polymer of Example 24 (176) | | | | Cl | 92.2[a] |
| 27 | hexamethylenediamine (3.48)<br>1,10-dibromodecane (9.0) | DMAC-MeOH-water 58:8:34 | 20 | reflux | Cl | 5.38[a] |
| 28 | hexamethylenediamine (3.87)<br>1,10-dibromodecane (12.6) | DMF-MeOH (1:1) | 24 | reflux | Cl | 8.4[a] |
| 29 | hexamethylenediamine (3.48)<br>1,10-dibromodecane (9.0) | MeOH-water (1:1) | 20 | 60 | Cl | 3.7[b] |
| 30 | hexamethylenediamine (3.48)<br>1,10-dibromodecane (9.0) | DMAC-MeOH (3:1) | 20 | 85 | Cl | 6.54[a] |
| 31 | hexamethylenediamine ((3.48)<br>1,10-dibromodecane (9.0) | DMAC-MeOH-water (66:17:17) | 20 | 84 | Cl | 5.35[a] |
| 32 | 1,8-diaminooctane (4.8)<br>1,10-dibromodecane (10.0) | DMF-MeOH (1:1) | 24 | reflux | Cl | 7.2[a] |
| 33 | 1,12-diaminododecane (6.66)<br>1,10-dibromodecane (10.0) | DMF-MeOH (1:1) | 24 | reflex | Cl | 8.7[a] |
| 34 | 1,7-diaminoheptane (4.33)<br>1,10-dibromodecane (10.0) | DMF-MeOH (1:1) | 24 | reflux | Cl | 6.6[a] |

TABLE 1-continued

Preparation of Polyamine Salts

| Example | Ingredients (wt. g) | Solvent (vol. ratio) | Total Solvent (mL) | Temperature °C. | Final Counterion | Polymer Yield (g) |
|---|---|---|---|---|---|---|
| 35 | 1,4-diaminobutane (2.93)<br>1,10-dibromodecane (10.0) | DMF-MeOH<br>(1:1) | 24 | reflux | Cl | 5.1[a] |
| 36 | 5,5'-methylenedifurfurylamine (2.5)<br>1,10-dibromodecane (3.65) | DMF-MeOH<br>(1:1) | 12 | reflux | Cl | 3.1[b] |
| 37 | hexamethylenediamine (46.4)<br>1,10-dichlorodecane (84.4) | MeOH | 260 | reflux | Cl | 123.7[b] |
| 38 | 1,3-diamino-2-hydroxypropane (3.0)<br>1,10-dibromodecane (10.0) | DMF:MeOH<br>(1:1) | 24 | reflux | Cl | 2.88[b] |

[a]purified polymer
[b]crude polymer
[c]gummy solid

[d]dimer diamine is $H_2N(CH_2)_n(CH_2CH)_m(CH_2)_{16-m-n}$—  —$(CH_2)_{16-m-n}—(CH=CH)_m(CH_2)_n—NH_2$ with substituent $\begin{array}{c} CH_3 \\ | \\ (CH_2)_x \\ | \end{array}$ on the ring

[e]change of counterion from Br to Cl

EXAMPLES 39–50

PREPARATIONS OF SUBSTITUTED POLYMERS

All substituted polymers were prepared in a similar manner. Polyamine was first synthesized and then used in all subsequent reactions. Polymer was synthesized, as in Example 1A or 1B, and stirred in 3 L of water until it was completely swollen (about 1 hour). At that time 400 ml of conc. ammonium hydroxide was added to the swollen polymer slurry and the mixture was stirred for at least 15 minutes. The product was then filtered and washed with water until the filtrate was neutral. After drying in a vacuum oven at 60° C., 54.6 g (88.7%) of polyamine was recovered.

EXAMPLE 39

Into a 100 mL three-necked round bottom flask was placed 20 mL DMF, 20 mL distilled water, 3.0 g of the polyamine prepared above and 2.32 g of 1-bromooctane. The mixture was refluxed at least 18 hours, after which time the contents of the flask were poured into 100 mL THF and stirred for 30 min. At this point, the product could be dried and weighed to determine extent of polymer substitution. The product was then added to 100 mL of a 10% HBr/water solution, stirred for at least 30 min., filtered, and washed with water until the filtrate was neutral to pH paper. The resulting polymer was then dried in a vacuum oven. The final yield of substituted polymer was 5.65 g (88.8%).

The following polymers were prepared in an identical manner using the following ingredients and quantities. See Table 2.

TABLE 2

| Example | Ingredients | Ing. Wt. (g) | Intermediate Wt. (g) | Polymer Final Wt. (g) |
|---|---|---|---|---|
| 40 | 2-(2-bromoethyl)-1,3-dioxane | 3.81 g | | |
| | polyamine | 5.0 g | — | 3.1 g |
| 41 | 2-(2-bromoethyl)-1,3-dioxolane | 3.53 g | | |
| | polyamine | 5.0 g | — | 8.24 g |
| 42 | BrCH$_2$CH$_2$OCH$_2$CH$_2$OCH$_2$CH$_2$OCH$_3$ | 1.62 g | | |
| | polyamine | 1.83 g | 2.79 g | 3.04 g |
| 43 | 1-bromohexadecane | 2.38 g | | |
| | polyamine | 2.0 g | 3.69 g | 3.9 g |
| 44 | 2-bromotridecane | 1.98 g | | |
| | polyamine | 2.0 g | 3.3 g | 3.65 g |
| 45 | 2-(bromoethyl)tetra-hydro-2H-pyran | 1.40 g | | |
| | polyamine | 2.0 g | 2.4 g | 2.88 g |
| 46 | 1-bromoundecane | 1.84 g | | |
| | polyamine | 2.0 g | 3.37 g | 3.73 g |
| 47 | 2-bromoeicosane | 2.82 g | | |

TABLE 2-continued

| Example | Ingredients | Ing. Wt. (g) | Intermediate Wt. (g) | Polymer Final Wt. (g) |
|---|---|---|---|---|
|  | polyamine | 2.0 g | 3.82 g | 4.08 g |
| 48 | 1-bromooctadecane | 2.60 g |  |  |
|  | polyamine | 2.0 g | 3.91 g | 4.25 g |
| 49 | 2-bromoethylmethylester | 1.08 g |  |  |
|  | polyamine | 2.0 g | 2.41 g | 2.80 g |
| 50 | 2-bromoethylethylether | 1.20 g |  |  |
|  | polyamine | 2.0 g | 2.46 g | 2.94 g |

EXAMPLE 51A

PREPARATION OF LARGER QUANTITY OF POLYMER

Into a 5 L three-necked round bottom flask equipped with an ice bath, overhead stirrer, reflux condenser, thermometer, and nitrogen inlet were added 1 L of DMF, 1 L of methanol, 386.7 g (3.33 mol) of hexamethylene diamine, and 1000.0 g (3.33 mol) of 1,10-dibromodecane. The resulting homogeneous solution was rapidly stirred without heating. Within 10 minutes the solution attained a temperature of 82° C. and refluxing occured. At this time ice was added to the ice bath to maintain a steady rate of reflux. After 20 minutes the initial heat of reaction dissipated and refluxing stopped. At this time, the ice bath was removed and a heating mantle was placed on the flask. The flask was then heated to maintain a steady reflux of the solvents. As the reaction solution was heated and stirred rapidly the viscosity of the reaction began to increase. Within 20 to 30 minutes after the beginning of heating the reaction, the mixture attained a viscosity which no longer allowed stirring. At this point, the agitator was stopped. The resulting swollen gelled mass was then gently heated at 30° C.–50° C. for an additional 18 to 21 hours. The gel was allowed to cool to room temperature and was scooped out of the reaction vessel. The gel was then put into a blender with an equal volume of 10% aqueous ammonium hydroxide and was ground in the blender. The resulting polymer was filtered and then slurried in 10% aqueous ammonium hydroxide for 1 hour. The polymer was then filtered and washed with distilled water until the filtrate was neutral. The polymer was then treated with 10 L of aqueous HCl (4 L conc. HCl+6 L water). The polymer was then filtered and washed with distilled water until the filtrate was neutral. The polymer was then washed with methanol and slurried in methanol. The slurried polymer was then loaded into 5 L Soxhlet extraction thimbles and extracted with methanol for 3–4 days and with water for an additional 3–4 days. The polymer was then removed from the extraction thimbles and dried in a vacuum oven at 60° C. for 2–3 days to yield the final polyammonium product containing chloride counter ion. Theoretical yield was 1089 g. Yield before extraction was 823 g. Yield after extraction was 800 g. The polymer could be ground in a blender or coffee mill to yield particle sizes of 30–500 microns. High speed hammer milling through a 100 mesh screen produced particle sizes in the range of 30–150 microns. Air jet micronizing produced particle sizes in the range of 30–150 microns. Grinding in an attritor in the presence of liquid nitrogen produced particle sizes as low as 1 micron. In most cases the material was coffee milled before use.

EXAMPLE 51B

PILOT SCALE PREPARATION OF POLYMERIC AMMONIM SALT Polymerization

To a jacketed horizontal mixer/reactor with a variable speed drive, 6.9 kg of 1,6-hexanediamine, 3.1 kg of sodium carbonate, 4.1 kg of DMAC and 3.4 kg of methanol were charged. In a separate glass-lined, agitated, vessel 19.6 kg of DBD, 12.2 kg of DMAC and 10.3 kg of methanol were charged. The mixture was then heated to 30° C. and held for 1.5 hours to dissolve the DBD. The DBD solution was fed from the glass-lined vessel to the horizontal mixer/reactor over 30 minutes. The horizontal mixer/reactor plows were turned on with the speed set at 155 rpm during the addition. The temperature in the horizontal mixer/reactor was held at 35°±5° C. during the transfer. The transfer line was flushed with an additional 0.4 kg of DMAC and 0.4 kg of methanol. The mixer/reactor was held at 35°±5° C. for 15 minutes after the transfer. Then the jacket outlet temperature was raised to 80° C. over 4 hours. The plow speed was reduced to 40 rpm when the outlet temperature reached 80° C. The horizontal mixer/reactor jacket outlet was maintained at 80° C. for another 16 hours. After the 16 hour hold, the contents of the horizontal mixer/reactor were cooled to 31° C. and discharged to a polyethylene-lined fiber drum. A total of 50.5 kg material was discharged from the horizontal mixer/ reactor.

Initial Size Reduction

The material from the horizontal mixer/reactor was added to 196 liters of USP water and wet milled continuously in an in-line continuous flow through mill. The milling loop started in a 50 gallon Nalgene hold tank, went to a pump, then the in-line continuous flow through mill, then through a heat exchanger and back to the Nalgene tank. Medium, fine and superfine heads were used in the in-line continuous flow through mill to reduce 98% of the particles to less than 850 micron. The milling took less than an hour.

Purification and Ion Exchange

The wet milled material was transfered to a glass-line agitated vessel. To the vessel containing the slurry 27.6 kg of 27% aqueous ammonium hydroxide was added. The mixture was heated to 50° C. After it reached 50° C. it was filter on an agitated filter. The filter media consisted of three 316 stainless steel screens. A 38 micron screen Was the primary filtration layer. The two other screens, which were 150 micron or larger, provided support. The wetcake in the filter was reslurried and filtered consecutively with 36 liters of USP water, a mixture of 44.5 kg of USP water and 5.4 kg of 27% ammonium hydroxide, 36 liters of USP water, a mixture of 44.5 kg of USP water and 5.4 kg of 27% ammonium hydroxide, and 36 liters of USP water. All reslurries and filtrations were done at 50 ° C.

The wetcake from the initial quench was split in four parts each part was treated separately as described below. In the agitated filters, each part was treated successively with acid, base, acid, base and acid. In each acid treatment, wetcake was reslurried in the agitated filter in 84 liters of USP water. Enough 32% aqueous HCL was added to lower the pH to less than 2.5. For base treatment, wetcake was reslurried in the agitated filter in 45 liters of USP water. Enough 27% aqueous ammonium hydroxide was added to raise the ph to greater than 9.5. After each base treatment the wetcake was washed with 36 liters of USP water. For the final acid treatment the pH was lower to 1.5 vs. the typical 2.5. The wetcake from the final acid treatment was washed until the pH was above 3.5. A total of 148.8 kg of wetcake was recovered from purification.

Final Size Reduction

The same milling apparatus used for initial milling was used for final milling except the heads of the in-line continuous flow through mill were changed. A fine and two superfine heads were installed. The 4 lots of wetcake recovered from purification were combined and milled in two lots. Each lot was was slurried in USP water prior to milling. For each kg of wetcake 0.5 kg of USP water was added. The slurry was milled for approximately 4 hours to get the particle size to 60–70 microns (50 percentile).

Drying

The two lots of wetmilled slurry were dried in a rotary vacuum dryer with 1.1 cubic feet of working capacity. Hot water (80°–90° C.) was aligned to the dryer jacket. Vacuum (22–26 inches of Hg) was aligned to the drying chamber. Drying took approximately 5 days to complete. 11.3 kg of dry DMP503 was recovered. The swell of the DMP503 was 13.0–13.6.

EXAMPLE 52

SWELLING OF POLYMER PRODUCED IN EXAMPLE 1 (Br⁻ ION))

To 0.5 g polyammonium bromide prepared in Example 1 was added 13 mL of distilled water. Within minutes the polymer swelled to completely absorb that volume of water. When the vial was inverted no liquid water poured. This behavior indicates at least a 26:1 (2600%) swell factor for this polymer.

EXAMPLE 53

DETERMINATION OF EXTENT OF BRANCHING/CROSSLINKING OF POLYMER PRODUCED AS IN EXAMPLE 1 (Br⁻ ION)

Polyammonium bromide prepared as described in Example 1 was placed in a 10 mm NMR tube. To this was added enough dioxane to slurry the polymer. Water (D$_2$O) was then added to swell the polymer. A $^{13}$C NMR spectra was then run on the sample. The following signals were observed for the carbon atoms immediately adjacent to the different possible nitrogen species contained in the polymer structure. 40.10 ppm (—C—NH$_3^+$) (10.24 integral units); 48.27 ppm (—C—NH$_2^+$—C—) (52.22 iu); 53.48 ppm

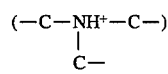

(35.07 iu); 58.75 ppm

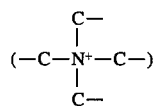

(2.57 iu).

Relative nitrogen abundance could be calculated as follows:

| | | |
|---|---|---|
| primary N (40.10 ppm) = | 10.24/1 = 10.24 | 21.0% |
| secondary N (48.27 ppm) = | 52.22/2 = 26.11 | 53.6% |
| tertiary N (53.48 ppm) = | 35.07/3 = 11.69 | 24.0% |
| quaternary N (58.75 ppm) = | 2.57/4 = 0.64 | 1.3% |

Thus, this polymer contained 53.6% secondary (straight chain) amines, 24.0% tertiary amines as either branch points or crosslinks, 21.0% primary amines as ends, and 1.3% quaternary amines as crosslinks or branch points.

In Vitro Binding of Bile Acids to Bile Acid Sequestrants

The binding of bile acids to the bile acid sequestrant crosslinked polymeric ammonium salts of the present invention may be measured using the procedures described below.

The following method was used to measure the equilibrium binding paramaters for the binding of various bile acids to the bile acid sequestrants of the present invention. The equilibrium binding of bile acids to bile acid sequestrants was determined using isotonic ionic conditions at 37° C., in order to roughly approximate physiological conditions. Carbon-14 ($^{14}$C) labeled bile acids dissolved in phosphate buffered saline (PBS) at pH 7 were prepared at 0.454, 0.555, 0.713, 1.000, 1.667, 5.000, 6.667, 10.0, 20.0 and 30.0 mM (45 nCi $^{14}$C/ml) concentrations. This series of reciprocal concentration levels were chosen to afford relatively even distribution of empirical data along the semilogarithmic saturation binding curves.

The bile acids were purchased from Sigma (St. Louis, Mo.) and the $^{14}$C labeled bile salts having a specific activity of approximately 50 mCi/mmole were obtained from E. I. du Pont de Nemours and Company, New England Nuclear (Billerica, Mass.).

Two mL of the prepared concentrations of bile acid were added to a selected amount (for example, 5.0 mg) of bile acid sequestrant to be tested, within a 10,000 mw cut-off ultrafiltration cup (Nihon Millipore, Yonezawa, Japan) and incubated overnight (16 hours) at 37° C.

Cholestyramine, which was tested for reference, was obtained from Sigma, St. Louis, Mo.

To determine the non-specific binding, the ten stock solutions of bile salts were added to empty ultrafiltration cups and incubated together with the total binding samples.

To separate bound and free bile acid the ultrafiltration cups were centrifuged at 3,500 RPM at 37° C. in a Du Pont RT6000 centrifuge to pass the solution of free bile acids into the outer tube. Two hundred μL of the separated binding tubes and the corresponding set of the stock solutions of total bile acid were counted for two minutes in a beta scintillation counter (Beckman, Palo Alto, Calif.) to detect $^{14}$C DPMs in 7 mLs of Formula 989 scintillation cocktail (E. I. du Pont de Nemours and Company, New England Nuclear, Billerica, Mass.).

The respective specific bound DPMs were determined from the counted total added $^{14}$C DPMs and derived total binding and non-specific binding DPMs. The specific bound DPMs were converted to specifically bound μmoles of bile salts at each dose level. The specific binding data was plotted on a saturation binding curve (specific bound μmoles of bile salts/mg of sequestrant versus the log of the free μmoles of bile salts/mL of solution) and the best-fit regression curve was determined using the relationship, Equation 1 below:

$$[\text{Bound}]=(B_{max}\times[\text{Free}]^n)/((K_d)^n+[\text{Free}]^n) \qquad \text{Equation 1}$$

where Bmax is the maximum amount of bile salt bound to sequestrant, Kd is the concentration of free bile salt at which there is half-maximal binding (i.e., an equilibrium dissociation constant) and n is a curve fitting parameter. Another model used was the ligand-ligand interaction model isotherm that is represented by Equation 2:

$$B=(B_{max}/2)\{1+((F/K_d)-1)/Sqrt[((F/K_d)-1)^2+4F/W\times K_d)]\} \qquad \text{Equation 2}$$

where F is the free bile acid concentration; W is the ligand ligand interaction parameter or cooperativity parameter; and Sqrt is the square root of the quantity in brackets. (See McGhee Von Hippel, J. Mol. Biol., 86: 469–489 (1974); Biophysical Chemistry, Part III, C. Cantor and P. Schimmel (1980), pages 878–885 and pages 1242–1251.)

Data for the binding of various bile acids to representative bile acid sequestrant polymers of the present invention is shown in Tables 3 and 4 below. In Tables 3 and 4, $B_{max}$ is presented in units of μmol of bile salt bound per mg of bile acid sequestrant and Kd is in units of mM.

The value $B_{max}/K_d$ is a measure of the binding efficiency of the bile acid sequestrant for the binding of bile acids, and reflects both the total number of binding sites or binding capacity and the binding affinity of the bile acid sequestrant for bile acid. The higher this number is, the more effective a bile acid sequestrant is predicted to be.

As shown in Tables 3 and 4, the bile acid sequestrant polymers of the present invention are substantially more effective in binding bile acids, in terms of both increased affinity and increased binding capacity, relative to cholestyramine.

In Table 4, the cholestyramine results were graphed using the Equation 1 and the other examples were graphed using Equation 2.

Substantially the same results are obtained for Bmax/Kd when the same data is analyzed using the above equation as when it is analyzed using Equation 1.

TABLE 3

In Vitro Equilibrium Binding of Bile Acids to Bile Acid Sequestrants

| Polymer of Ex. No. | Bile Acid | Bmax | Kd | Bmax/Kd |
|---|---|---|---|---|
| Cholestyramine | cholate | 3.38 | 7.35 | 0.46 |
| | taurocholate | 2.84 | 2.15 | 1.32 |
| | glycocholate | 2.93 | 7.38 | 0.40 |
| | chenodeoxycholate | 3.13 | 0.494 | 6.34 |
| 1A | cholate | 4.37 | 2.25 | 1.94 |
| | taurocholate | 4.62 | 1.78 | 2.60 |
| | glycocholate | 3.89 | 1.84 | 2.11 |
| | chenodeoxycholate | 3.25 | 0.163 | 19.9 |
| 37 | cholate | 5.13 | 1.47 | 3.49 |
| | taurocholate | 4.82 | 1.27 | 3.80 |
| | glycocholate | 5.11 | 1.84 | 2.78 |
| | chenodeoxycholate | 4.49 | 0.201 | 22.3 |
| 8 | cholate | 4.70 | 1.16 | 4.05 |
| | taurocholate | 4.18 | 1.38 | 3.03 |
| | glycocholate | 3.83 | 1.60 | 2.39 |
| | chenodeoxycholate | 4.77 | 0.380 | 12.6 |

TABLE 3-continued

In Vitro Equilibrium Binding of Bile Acids to Bile Acid Sequestrants

| Polymer of Ex. No. | Bile Acid | Bmax | Kd | Bmax/Kd |
|---|---|---|---|---|
| 9 | cholate | 4.16 | 2.81 | 1.48 |
| | taurocholate | 4.06 | 3.40 | 1.19 |
| | glycocholate | 4.22 | 3.76 | 1.12 |
| | chenodeoxycholate | 3.81 | 0.193 | 19.7 |
| 11 | cholate | 3.85 | 1.80 | 2.14 |
| | taurocholate | 3.23 | 3.45 | 0.94 |
| | glycocholate | 3.39 | 3.94 | 0.86 |
| | chenodeoxycholate | 3.20 | 0.125 | 25.6 |
| 40 | cholate | 3.42 | 1.92 | 1.78 |
| | taurocholate | 2.97 | 1.49 | 1.99 |
| | glycocholate | 2.96 | 2.19 | 1.35 |
| | chenodeoxycholate | 3.19 | 0.170 | 18.8 |
| 41 | cholate | 3.11 | 1.88 | 1.65 |
| | taurocholate | 2.80 | 2.80 | 1.00 |
| | glycocholate | 2.93 | 2.20 | 1.33 |
| | chenodeoxycholate | 3.17 | 0.227 | 14.0 |
| 48 | cholate | 4.65 | 2.25 | 2.07 |
| | taurocholate | 3.83 | 1.92 | 1.99 |
| | glycocholate | 3.65 | 2.38 | 1.53 |
| | chenodeoxycholate | 4.17 | 0.165 | 25.3 |

TABLE 4

In Vitro Binding of Cholate to Bile Acid Sequestrants

| Polymer of Example | Swell Factor | Bmax | Kd | Bmax/Kd |
|---|---|---|---|---|
| Cholestyramine* | | 3.38 | 7.35 | 0.46 |
| 24** | 14.4 | 4.33 | 1.43 | 3.03 |
| 25 | | 4.51 | 1.33 | 3.39 |
| 26 | 21.6 | 4.45 | 1.19 | 3.74 |
| 27 | 2.6 | 1.70 | 1.45 | 1.17 |
| 28 | 4.9 | 4.98 | 1.11 | 4.49 |
| 29 | 1.3 | 2.33 | 1.13 | 2.06 |
| 30 | 14.6 | 5.20 | 1.29 | 4.03 |
| 32 | 12.1 | 5.34 | 1.02 | 5.24 |
| 33 | 0.1 | 2.68 | 0.61 | 4.39 |
| 34 | 11.9 | 4.05 | 0.96 | 4.22 |
| 35 | 21.5 | 5.88 | 1.25 | 4.70 |
| 38 | 135.6 | 5.26 | 0.90 | 5.84 |
| 45 | | 1.31 | 1.02 | 1.28 |
| 46 | | 2.96 | 2.21 | 1.34 |
| 47 | | 3.78 | 1.53 | 2.47 |
| 50 | | 3.70 | 1.56 | 2.37 |

*Binding data was plotted on a curve according to Equation 1.
**Binding data for Examples 24, 25, 26, 27, 28, 29, 30, 32, 33, 34, 35, 38, 45, 46, 47, and 50 were plotted on a curve according to the ligand-ligand interaction isotherm of Equation 2.

In Vivo Plasma Cholesterol Lowering Activity of Bile Acid Sequestrants

The in vivo plasma cholesterol lowering activity of the bile acid sequestrant polymers of the present invention were evaluated in the animal models described below.

Plasma Cholesterol Lowering in Hamsters Administered Bile Acid Seauestrants

The plasma cholesterol lowering effect of representative bile acid sequestrant polymers of the present invention is shown in Table 5 below. Male hamsters were fed for 2 weeks the selected bile acid sequestrant to be tested and the total cholesterol concentration in the plasma was determined. Total serum cholesterol was measured using a cholesterol oxidase assay on a Dimension® clinical analyzer. The sequestrants were given orally by mixing in the animal feed.

The hamsters were given 11 g of Agway rodent chow per day for 2 weeks that contained varying weights of sequestrant. Results for 0.25, or 0.3 weight % sequestrant (for example 0.3 weight % is 0.033 g sequestrant per 11 g of feed are shown). The polymer was ground and mixed with the feed.

In each study, 7 animals were dosed with the sequestrant. The % decrease in cholesterol levels was calculated by subtracting the average total cholesterol levels at 2 weeks of sequestrant treatment, from the average total cholesterol levels in the animals before treatment (week 0).

In Table 5, where a single 7 animal study was carried out, the uncertainty in the measured cholesterol lowering is expressed as the SEM (or standard deviation (SD)) for a particular study (i.e., for 7 animals). In Table 5, the SEM (or SD) for the study at Week 0 and Week 2 is given and the SEM (or SD) is also expressed as a % of the average value of total cholesterol. Also given in Table 5 is the % decrease in total cholesterol level and the average % SEM (or SD) for Weeks 0 and 2.

tions are not excluded from the present invention, so long as they do not prevent the benefits of the invention from being realized.

EXAMPLES 54 TO 73

Sequestrant polymers were made by a procedure similar to that used in Example 1. The starting materials and synthesis conditions are given in Table 7.

BINDING ABILITY OF THE SEQUESTRANTS OF EXAMPLES 54 TO 73

The efficacy of these sequestrants was tested using the "Sequestrant Glycocholate Binding Assay", the procedure for which is given below. In Table 8 the results of this assay are given for the sequestrants of Examples 54 to 73. The higher the "% Bound Glycocholate", the better the efficacy of the sequestrant. For comparison purposes, results from Cholestyramine and a sequestrant prepared according to the TABLE 5[a]

Plasma Cholesterol Lowering in Hamsters by Bile Acid Sequestrants
Total Cholesterol (ml/dg)
(± SEM or SD)

| Polymer of Example | Dose (weight %) | Week 0 | % Error | Week 2 | % Error | % Decrease in Total Cholesterol | Avg % Error |
|---|---|---|---|---|---|---|---|
| Cholestyramine | 0.3 | 171 ± 11* | ±6.4 | 150 ± 13* | ±8.7 | 12 | ±7.6* |
| 1A | 0.25 | 178 ± 4 | ±2.2 | 129 ± 3 | ±2.3 | 28 | ±2.3 |
| 1A | 0.3 | 167 ± 16* | ±9.6 | 127 ± 8* | ±6.3 | 24 | ±8.0* |
| 37 | 0.25 | 178 ± 7 | ±3.9 | 122 ± 2 | ±1.6 | 31 | ±2.8 |

[a]The total cholesterol levels are the average values for 7 animals. The value following ± is the standard error of the mean (SEM) except where marked with asterisk (*), where it is a standard deviation (SD).

Cholesterol Lowering in Rabbits Treated with Bile Acid Sequestrant

The cholesterol lowering efficacy of the polymer of Example 25 was tested in male New Zealand rabbits. As shown in Table 6 below, following 1 week and 2 weeks of treatment of rabbits with this polymer at 250 mg/kg of total body weight per day, the plasma total cholesterol levels in the animals were significantly decreased. Table 6 shows the mean % decrease in total plasma cholesterol levels for 5 animals (the SEM is given following ±). The bile acid sequestrant was administered by being mixed with the animal feed and being fed to the animals. Total serum cholesterol was measured using a cholesterol oxidase assay on a Dimension clinical analyzer.

TABLE 6

Rabbit Plasma Cholesterol Lowering After
1 Week and 2 Weeks of Bile Acid Sequestrant Treatment

| | % Decrease in Total Cholesterol (± SEM) | |
|---|---|---|
| | 1 Week | 2 Weeks |
| no bile acid sequestrant | 7 ± 10 | 17 ± 8 |
| cholestyramine | 14 ± 11 | 17 ± 13 |
| Polymer of Example 25 | 43 ± 11 | 42 ± 10 |

In the present disclosure it should be understood that the specified materials and conditions are important in practicing the invention but that unspecified materials and condiprocedure of Example 25 are also given.

SEQUESTRANT GLYCOCHOLATE BINDING ASSAY

A. Initial Binding Assay

Each polymer was weighed directly into a Millipore® ultra filtration cup (10,000 NML low binding cellulose). The weight added to each cup was around 5 mg/cup with the actual weight being recorded and each polymer was weighed into 3 cups. A 10 mM glycocholic acid solution (GC) was made with phosphate buffered saline (PBS) at a pH of 7, and kept at 37° C. To each cup, 2 ml of the above solution was added. This was done in sets of no more than 15 cups. Once the bile acid was added to the cups the cups were mixed with a vortex mixer and placed in a centrifuge. The cups were spun in a Sorvall® RT6000 centrifuge at 3500 RPM (setting #10) at 37° C. for 10 minutes.

B. 18 Hour Assay

Each polymer was weighed directly into the Millipore ultra filtration cups (10,000 NML low binding cellulose). The weight added to each cup was around 5 mg/cup with the actual weight being recorded and each polymer was weighed into 3 cups. A 10 mM glycocholic acid solution (GC) was made with phosphate buffered saline (PBS) at a pH of 7. To each cup, 2 mL of the above solution was added. The cups were incubated in an orbital dry air shaker at 37° C. for between 18 to 20 hours. After incubation the cups were spun in the Sorvall RT6000 centrifuge at 3500 RPMS (setting #10) at 37° C. for 1 hour or until at least 200 μl of solution had been eluted.

The reagents were bought as a kit from Sigma Chemical Co., St. Louis, Mo. 63178, Bile Acid Diagnostic Kit #450-A. Reagents were gently reconstituted with water, 10 ml for reagent A and 5 ml for reagent B. They were mixed by inverting, not shaking. The test reagent was maded by mixing reagent A with reagent B at a volume ratio of 4:1. For each sample 0.5 ml of the test reagent was needed. The test reagent was warmed to 37° C. by placing it in a 37° C. water bath about 15 minutes before it was needed. The assay was performed in 6 ml polypropylene test tubes. Each sample was diluted so as to be in the linear range of the assay. The bile acid salt filtrate samples and the 10 mM GC were first diluted 10 times, 100 μl plus 900 μl PBS. Each sample was done in duplicate so that for each example there were six samples. PBS was used as a zero control and the Absorbance from the average of 6 PBS samples was subtracted from all other samples. The 10 mM GC was diluted by a total factor of 50 to be at the maximum range of the assay, which is 200 μM, and six samples were tested. The samples were diluted by a total factor of 40. Two hundred μl of sample was needed for the assay. Since the samples were first diluted by 10 then diluted by 4, 50 μl of diluted sample plus 150 μl of PBS was assayed. For the 10 mM GC samples, they were also diluted first by 10 and then diluted by 5, therefore 40 μl of the diluted sample and 160 μl of PBS was assayed. For the bile acid zero controls, 200 μl of PBS was assayed. At this point all samples were treated the same. The assay was performed in batches of no more than 70 tubes. The samples were placed in the 37° C. water bath. Using a repeat pipetter 0.5 ml of test reagent was added to each tube at a consistent pace. The timer was started at the same time that the test reagent was added to the first tube. After 5 minutes the reaction was stopped by adding 100 μl of 1.33M phosphoric acid at the same pace that the test reagent was added. The samples were poured into 1.5 ml plastic cuvets and read on a spectrometer at 530 nm. Samples were only stable for one hour.

Using absorbance data obtained from standard GC solutions, the percent of bile acid bound per 5 mg of sequestrant was calculated. Cholestyramine was tested in every assay for comparative purposes. The binding assay for a polymer was repeated if the three samples were not within the standard error of about 5% to 10% compared to each other.

TABLE 7

| Ex. No. | Composition | Wt (g) | Solvent (Vol. ratio) | Total Solvent (mL) | Temp | Final Counter Ion | Polymer Yield (g) |
|---|---|---|---|---|---|---|---|
| 54 | 1,9-Dibromonane<br>1,4-Diaminobutane | 11.08<br>3.41 | DMAC/MeOH<br>1:1 | 26 | reflux | Cl⁻ | 6.19 |
| 55 | 1,11-Dibromoundecane<br>1,4-Diaminobutane | 11.07<br>3.10 | DMAC/MeOH<br>1:1 | 21 | reflux | Cl⁻ | 7.12 |
| 56 | 1,12-Dibromododecane<br>1,4-Diaminobutane | 11.07<br>2.97 | DMAC/MeOH<br>1:1 | 21 | reflux | Cl⁻ | 4.79 |
| 57 | 1,3-Butadiene Diepoxide<br>1,8-Diaminooctane | 3.98<br>6.68 | MeOH | 11 | reflux | Cl⁻ | 10.34 |
| 58 | 1,3-Butadiene Diepoxide<br>1,9-Diaminononane | 3.81<br>7.00 | MeOH | 11 | reflux | Cl⁻ | 10.14 |
| 59 | 1,3-Butadiene Diepoxide<br>1,10-Diaminodecane | 3.44<br>6.88 | MeOH | 10 | reflux | Cl⁻ | 9.81 |
| 60 | 1,2,7,8-Diepoxyoctane<br>1,8-Diaminooctane | 4.37<br>4.42 | MeOH | 13 | reflux | Cl⁻ | 8.50 |
| 61 | 1,2,7,8-Diepoxyoctane<br>1,10-Diaminodecane | 3.70<br>4.47 | MeOH | 10 | reflux | Cl⁻ | 7.63 |
| 62 | 1,2,7,8-Diepoxyoctane<br>1,8-Dibromooctane<br>1,8-Diaminooctane | 1.17<br>6.72<br>4.74 | DMAC/MeOH<br>1:1 | 19 | reflux | Cl⁻ | 8.20 |
| 63 | 1,2,7,8-Diepoxyoctane<br>1,8-Dibromooctane<br>1,8-Diaminooctane | 2.29<br>4.37<br>4.63 | DMAC/MeOH<br>1:1 | 17 | reflux | Cl⁻ | 8.21 |
| 64 | trans-1,4-Dichloro-2-butene<br>1,8-Diaminooctane | 4.86<br>5.64 | DMAC/MeOH<br>1:1 | 16 | reflux | Cl⁻ | 6.48 |
| 65 | trans-1,4-Dichloro-2-butene<br>1,9-Diaminononane | 4.84<br>6.16 | DMAC/MeOH<br>1:1 | 16 | reflux | Cl⁻ | 7.03 |
| 66 | trans-1,4-Dichloro-2-butene<br>1,10-Diaminodecane | 4.61<br>6.39 | DMAC/MeOH<br>1:1 | 16 | reflux | Cl⁻ | 6.55 |
| 67 | 1,10-Dibromodecane<br>Tris(2-aminoethyl)amine | 7.94<br>3.84 | DMAC/MeOH<br>1:1 | 18 | reflux | Cl⁻ | 7.66 |
| 68 | 1,3-diamino-2-hydroxypropane<br>1,8-dibromooctane | 3.0<br>9.1 | DMF/MeOH<br>1:1 | 16 | reflux | Cl⁻ | 4.9 |
| 69 | hexamethylenediamine<br>hexylamine<br>1,10-dibromodecane<br>sodium carbonate | 2.9<br>0.84<br>10.0<br>3.5 | DMF/MeOH<br>1:1 | 24 | reflux | Cl⁻ | 6.7 |
| 70 | hexamethylenediamine<br>4-(aminomethyl)piperidine<br>1,10-dibromodecane<br>sodium carbonate | 1.93<br>1.90<br>10.0<br>3.5 | DMF/MeOH<br>1:1 | 24 | reflux | Cl⁻ | 7.7 |
| 71 | 1,4-butanediamine<br>2-methylpentamethylene diamine<br>1,10-dibromodecane | 1.47<br>1.93<br>10.0 | DMF/MeOH<br>1:1 | 24 | reflux | Cl⁻ | 6.3 |
| 72 | divinylbenzene<br>hexanediamine<br>1,10-dibromodecane<br>n-BuLi1.6M (in hexane) | 5.0<br>4.46<br>3.41<br>2.26 mL | THF | 20 | reflux | Cl⁻ | 2 |

TABLE 7-continued

| Ex. No. | Composition | Wt (g) | Solvent (Vol. ratio) | Total Solvent (mL) | Temp | Final Counter Ion | Polymer Yield (g) |
|---|---|---|---|---|---|---|---|
| 73 | Jeffamine ® EDR-192 ($H_2NCH_2CH_2OCH_2CH_2OCH_2CH_2OCH_2CH_2NH_2$) 1,10-dibromodecane diethylenetriamine | 3.2 10.0 1.7 | DMF/MeOH 1:1 | 24 | reflux | Cl⁻ | |

TABLE 8

% BOUND GLYCOCHOLATE OF VARIOUS SEQUESTRANTS

| Polymer of Ex. No. | Swell Factor | % Bound Glycocholate |
|---|---|---|
| Cholestryamine[c] | — | 44–52[a] 37–44[b] |
| Polymer by method 25[d] | — | 80.5[a] 81.7[b] |
| 54 | 13.6 | 76.9[a] |
| 55 | 11.9 | 63.2[a] |
| 56 | 19.9 | 52.2[a] |
| 57 | 11.1 | 73.8[a] |
| 58 | 13.2 | 72.4[a] |
| 59 | 11.4 | 69.9[a] |
| 60 | 16.2 | 67.2[a] |
| 61 | 9.1 | 75.8[a] |
| 62 | 18.1 | 71.9[a] |
| 63 | 12.9 | 73.9[a] |
| 64 | 11.2 | 74.0[a] |
| 65 | 8.9 | 73.8[a] |
| 66 | 12.0 | 71.0[a] |
| 67 | 29.8 | 58.7[a] |
| 68 | 4.4 | 66.2[b] |
| 69 | 24.0 | 75.1[b] |
| 70 | 22.5 | 82.6[b] |
| 71 | 50.8 | 79.9[a] |
| 72 | 39.1 | 80.2[b] |
| 73 | — | 60.2[a] |

[a]After 10 min.
[b]After 18 hr.
[c]$B_{max}$ (μmoles/mg) = 3.13; Kd(mM) = 7.72
[d]$B_{max}$ (μmoles/mg) = 5.83; Kd(mM) = 1.58

EXAMPLES 74–97

In all of these Examples,! bile acid sequestrants were made in the presence of templates. $B_{max}$ and $K_d$ were determined by the ligand-ligand method of Equation 2, as in Table 4. Percent in vitro binding (of glcocholate) was determined the same way as for Table 8.

The following abbreviations are used:
DMAC—N,N-dimethylacetamide
DMF—N,N-dimethylformamide

EXAMPLE 74

Into a 1 L roundbottom flask equipped with a heating mantle, reflux condenser, nitrogen inlet, and overhead stirrer was added 240 mL of methanol, 240 mL of DMF, and 100 g of sodium chloride. The mixture was stirred to form a slurry, after which time 77.2 g (0.6667 mol) of hexamethylenediamine and 200 g (0.6667 mol) of 1,10-dibromodecane were added. The mixture was heated with stirring at reflux for ~45 minutes until a firm gel formed. After gel formation the stirring was discontinued and the gel was left to stand at room temperature overnight. The gel was then chopped/washed with aqueous ammonium hydroxide, neutralized with water, acidified with HCl (60% conc. HCl/40% water), and washed till neutral with water. The product was then soxhlet extracted for 4 days with methanol and 3 days with water. The resulting product was then dried in a 60° C. vaccum oven under a nitrogen purge and ground in a coffee mill to yield 126 g (57.8%) of white polymer. The swell measured to be 16.6 in water. $B_{max}$ 5.24; $K_d$ 1.13; $B_{max}/K_d$=4.64.

EXAMPLE 75

Into a 2 L three-necked roundbottom flask was added 300 mL of methanol, 300 mL of DMAC, and 66.7 g of hydroxypropyl cellulose (HPC) (Klucel JF). The mixture was stirred under a nitrogen atmosphere until the HPC dissolved. After that time 71.2 g (0.613 mol) of hexamethylene diamine and 32.5 g (0.307 mol) of sodium carbonate were added, and the mixture was stirred for about 5 minutes. After stirring, 1,10-dibromodecane (184.0 g, 0.613 mol) was then added, and the mixture was heated to 80° C. and maintained at that temperature until gelation occurred (~55 min). The stirrer was then stopped and the polymer was allowed to stand at 35° C. overnight. The polymer was then removed from the flask and ground in a blender with an equal volume of 10% ammonium hydroxide. After filtration and washing, the polymer was slurried in 10% ammonium hydroxide for one hour. It was then filtered and washed until neutral, and then slurried in 100 mL 4N HCl for about 30 minutes. The polymer was filtered and again washed until neutral, giving a swollen gel. The gel was purified by extraction in a Soxhlet apparatus for seven days with methanol. The gel was dried for 3 days in a 60° C. vacuum oven, giving 145.1 g (72.6%) of the polymer as a pale yellow solid. The swell was 12.5 in water. $B_{max}$ 4.74; $K_d$ 1.22; $B_{max}/K_d$=3.88.

Residual HPC could be monitored in the final polymer by IR (bands at ~1080 cm⁻¹ for HPC) and C-13 NMR (broad peak ~75–80). If a thorough wash is accomplished, virtually no residual HPC is detected by these methods.

EXAMPLE 76

Into a 3 L three-necked round bottom flask equipped with a heating mantle, overhead stirrer, condenser, and nitrogen inlet was added 120 g of poly(2-hydroxyethylmethacrylate) (poly(HEMA)), 360 g of DMF and 360 g of methanol. This mixture was :stirred for an hour at 40° C. Once the poly-(HEMA) was completely dissolved, 120 g (1.03 mol) 1,6-hexanediamine, 310.2 g (1.03 mol) 1,10-dibromodecane and 120 g (1.13 mol) sodium carbonate were added to the flask. The contents of the flask were stirred rapidly and heated to 80° C. The reaction mixture formed a slurried gel after ~30 minutes. The stirring rate was reduced and the flask heated for an additional 6 hours. The contents of the flask were then mixed with aqueous ammonium hydroxide and agitated for an hour at room temperature. The polymer was then filtered and washed with water repeatedly. The polymer was then transferred to a large beaker and stirred with aqueous hydrochloric acid for about 30 minutes. The polymer was then filtered and washed with water repeatedly. The swollen polymer was slurried with methanol and transferred into 3 L thimbles for soxhlet extraction. Polymer was first extracted with methanol and then with water for 3 days each. The extracted polymer was dried in a vacuum oven at ~60° C. The dried polymer was ground to yield 243 g (72%) of desired product. The polymer exhibited a swell of 18.7 in water. $B_{max}$ 4.86; $K_d$ 1.29; $B_{max}/K_d$=3.77.

EXAMPLE 77

Into a 100 mL flask equipped with a heating mantle, reflux condenser, nitrogen inlet, and overhead stirrer was added 12 mL DMF, 12 mL methanol, and 20.0 g of cholesteryl chloride. The mixture was stirred to form a slurry; after which time 3.86 g (0.0333 mol) of hexamethylene diamine and 10.0 g (0.0333 mol) of 1,10-dibromodecane were added. The mixture was heated to reflux and stirred. After approximately 1 hour a gel formed. The gel was stirred with heating for an additional 3 hours and then allowed to stand at room temperature overnight. The resulting polymer was chopped in a blender with methylene chloride, filtered, rinsed with additional methylene chloride, washed with methanol and then water. The polymer was then stirred with 50% aqueous ammonium hydroxide, washed with water, and reacidified with aqueous HCl. The material was then washed with water till the filtrate was neutral. This washing treatment was repeated an additional 4 times and the polymer was dried in a 60° C. vacuum oven under a nitrogen purge to yield 7.33 g (67.3%) of the desired polymer. The swell was found to be 21.5 in water.

EXAMPLE 78

Into a 2 L three necked round bottom flask was added 157 mL methanol, 157 mL DMAC, and 40.0 g hydroxypropyl cellulose (HPC) (Klucel LF). The mixture was stirred until the HPC dissolved. To this solution was added 47.25 g (0.537 mol) 1,4-diaminobutane and 56.91 g (0.537 mol) sodium carbonate, and the mixture was stirred for about 5 minutes. At this point 161.07 g (0.537 mol) of 1,10-dibromodecane was added, and the mixture was heated to reflux and maintained at that temperature until gelation occurred (~34 min). The resulting gel was heated at 30° C. overnight. The polymer was then removed from the flask and ground in a blender with an equal volume of 10% ammonium hydroxide. After filtration and washing, the polymer was slurried in 10% ammonium hydroxide for one hour. It was then filtered and washed until neutral, and then slurried in 1 L of 4N HCL for about 30 min. The polymer was filtered and again washed until neutral, giving a swollen gel. The gel was slurried in methanol, filtered, and then finally slurried in water and filtered. This cycle, starting with the ammonium hydroxide step, was repeated 4 times. The gel was dried for 3 days in a 60° C. vacuum oven, giving 109.16 g (68.2%) of the polymer as a pale yellow solid. The swell was 14.8 in water. $B_{max}$ 6.55; $K_d$ 2.09; $B_{max}/K_d$=3.13.

EXAMPLE 79

Into a 100 mL round bottom flask was added 11.5 mL of methanol, 11.5 mL of DMAC, and 3.0 g of polyvinylpyrolidone (24,000 MW) (PVP). The mixture was stirred until the PVP dissolved. At that point 4.27 g (0.0368 mol) of hexamethylene diamine and 11.04 g (0.0368 mol) of 1,10-dibromodecane were added. The mixture was reared to reflux and stirred until a firm gel formed (~39 min). After gel formation the stirring was discontinued and the gel was left to stand at room temperature overnight. The gel was then chopped/washed with aqueous ammonium hydroxide, neutralized with water, acidified with HCl, and washed till neutral with water. The product was then Soxhlet extracted for 3 days with methanol and 3 days with water. The resulting product was then dried in a 60° C. nitrogen purged vacuum oven and ground in a coffee mill to yield 8.12 g (67.7%) of the desired polymer. The swell measured to be 9.1 in water; in vitro binding of glycocholate was 71.6%.

EXAMPLE 80

Into a 100 mL round bottom flask was added 15 g DMF, 7.5 g methanol, and 6.0 g of polyvinylacetate (PVAc). These ingredients were stirred until the PVAc dissolved after which time 2 g of DMF, 3 g of methanol, 15.5 g 1,10-dibromodecane (0.0517 mol), and 6.0 g hexamethylenediamine (0.0517 mol) were added to the flask. The mixture was heated to 80° C. and stirred for 30 min. After this time 2 g of sodium carbonate was added to the reaction mixture. After an additional 30 min. of heating and stirring a gelled product formed. After allowing the gel to remain in the reaction flask overnight, the gel was removed and chopped/washed with aqueous ammonium hydroxide. The polymer was then washed with water and reacidified with aqueous HCl. The gel was again washed with water and extracted in a Soxhlet apparatus first with methanol for 3 days and then with water for 3 days. The polymer was then dried in a nitrogen purged vacuum oven at 60° C. and ground in a coffee mill to yield 14.6 g of desired product. The swell measured 14.9 in water and in vitro binding of glycocholate was 79.4%.

EXAMPLES 81–97

The polymers of Examples 81–97 were prepared in essentially the same manner as Example 74 except that the quantities used were 1/20th of those used in the original example (e.g., 12 mL of methanol, 12 mL of DMF, 3.86 g of hexamethylenediamine, and 10 g of 1,10-dibromodecane). The template and the quantity of template used are shown in Table 9 along with the resulting swell and in vitro glycocholate binding data (10 min. test):

TABLE 9

| Example No. | Template (g) | Water Swell | % Binding Glycolate |
| --- | --- | --- | --- |
| 81 | NaCl (2) | 26.9 | 73.9 |
| 82 | NaCl (10) | 21.2 | 70.2 |
| 83 | NaCl (20) | 26.0 | 70.4 |
| 84 | NaCl (30) | 26.6 | 71.4 |
| 85 | NaCl (40) | 30.6 | 75.7 |
| 86 | NaCl (50) | 20.2 | 71.7 |
| 87 | Na citrate (20) | 14.4 | 72.4 |
| 88 | methyl cholate (13.8) | 23.6 | 82.6 |
| 89 | poly(tetramethylene glycol) (10) | 19.4 | 80.3 |
| 90 | rhamsan gum (10) | 8.5 | 75.6 |
| 91 | zein (2.7) | 20.2 | 74.9 |
| 92 | wheat starch (10) | 15.8 | 69.1 |
| 93 | amaizo (10) | 20.0 | 77.2 |
| 94 | corn amylose (10) | 19.6 | 67.0 |
| 95 | pomosin pectin (10) | 4.0 | 60.4 |
| 96 | trehalose (12.6) | 14.8 | 76.5 |
| 97 | sodium carbonate (10) | 20.6 | 72.4 |

In Vivo Testing

Groups of 5 male Golden Syrian hamsters were dosed with 100 mg and 250 mg of sequestrant per kg of body weight per day for 2 weeks. The sequestrant was mixed with standard hamster chow. Total serum cholesterol was measured by Dimension methodology before dosing to give a baseline for each animal. After the 2 week dosing, total serum cholesterol was measured again for each animal and the percentage change in total serum cholesterol from baseline was calculated. Results are given in Table 10.

TABLE 10

| Sequestrant of Example | % Change from Baseline ± SEM | |
|---|---|---|
| | 100 mg/kg/day | 250 mg/kg/day |
| 74 | −16.5 ± 2.6 | −24.7 ± 1.3 |
| control* | −4.2 ± 1.8 | −12.5 ± 3.6 |
| 75 | −11.3 ± 2.1 | −12.0 ± 3.9** |
| control | −5.1 ± 3.2 | −8.4 ± 5.9** |
| 76 | −10.0 ± 4.3 | −23.3 ± 3.3 |
| control* | −5.8 ± 3.1 | −11.6 ± 2.5 |
| 77 | −17.1 ± 2.4 | −25.9 ± 0.6 |
| control* | −13.6 ± 3.4 | −18.9 ± 1.0 |
| 78 | −12.6 ± 5.1 | −18.1 ± 2.2 |
| control* | −8.1 ± 2.1 | −15.1 ± 2.3 |

*The "control" was a polymer prepared in the same manner as Examples 74–78 but without template present. As shown, the serum cholesterol % changes were variable for each group of animals tested.
**Tested at 200 mg/kg/day.

What is claimed is:

1. A solution polymerization process for preparing a crosslinked polymeric ammonium salt or a pharmaceutically acceptable salt form thereof, said crosslinked polymeric ammonium salt comprising ammonium nitrogen atoms linked by segments to other ammonium nitrogen atoms, wherein:

about 25% or more of the segments which link ammonium nitrogen atoms are group Y wherein each Y is independently —$(CR^1R^2)_b$— wherein b is an integer of 7 to about 20, and each $R^1$ and $R^2$ is independently $C_1$–$C_{20}$ alkyl or hydrogen;

the remainder of the nitrogen atoms are linked by segments Z wherein each Z is independently a hydrocarbylene radical containing 2 to 50 carbon atoms, said hydrocarbylene radical optionally containing one or more hydroxyl, ether, amino, thioether, keto, or silyl groups or heterocyclic rings;

wherein about 25% or more of the ammonium nitrogen atoms are secondary ammonium nitrogen atoms;

wherein said crosslinked polymeric ammonium salt is insoluble in water, is a bile acid sequestrant with a $B_{max}/K_d$ value for cholate of greater than 0.75; and wherein at least some of said ammonium nitrogen atoms are part of a crosslinked network; said process comprising:

reacting in a suitable solvent a bifunctional organic compound of the formula X—Y—X or X—Z—X, where X is a leaving group suitable for amine alkylations, and a diamine, of the formula $H_2N$—Y—$NH_2$ or $H_2N$—Z—$NH_2$, in the presence of an aqueous solution soluble organic polymer template to form a gel; and removing the template from the gel after the formation of the gel.

2. A process of claim 1 wherein the bifunctional organic compound and the diamine are present in the reaction in a mole ratio of 0.9 to 1.4.

3. A process of claim 1 wherein:
the aqueous solution soluble organic polymer template is selected from the group consisting of:

poly(2-hydroxyethyl methacrylate), polyvinylpyrrolidone, potato starch, wheat starch, pea starch, gellan gum, xanthan gum, amaizo, amylose, zein, pectin, ethylcellulose, methylcellulose, hydroxypropylcellulose, and carboxymethylcellulose;

and the template is present in an amount of 5 to 500% by weight relative to the total reaction weight in the absence of template.

4. A process of claim 3 wherein the bifunctional organic compound is selected from: 1,10-dibromodecane, 1,12-dibromododecane, 1,8-dibromooctane, 1,18-dibromooctadecane, 1,9-dibromononane, 1,7-dibromoheptane, 1,8-dibromo-3-ethyloctane, 1,9-dibromodecane, 1,10-dichlorodecane, 1,12-dichlorododecane, 1,8-dichlorooctane, 1,18-dichlorooctadecane, 1,9-dichlorononane, 1,7-dichloroheptane, 1,8-dichloro-3-ethyloctane, 1,9-dichlorodecane, 1,10-diiododecane, 1,12-diiodododecane, 1,8-diiodooctane, 1,18-diiodooctadecane, 1,9-diiodononane, 1,7-diiodoheptane, 1,8-diiodo-3-ethyloctane, 1,9-diiodododecane, 1,9-diepoxydecane, 1,11-diepoxydodecane, 1,7-diepoxyoctane, 1,17-diepoxyoctadecane, 1,8-diepoxynonane, 1,6-diepoxyheptane, 1,7-diepoxyoctane, and 1,7-diepoxy-3-ethyloctane, 1,9-diaziridinodecane, 1,11-diaziridinododecane, 1,7-diaziridinooctane, 1,17-diaziridinooctadecane, 1,8-diaziridinononane, 1,6-diaziridinoheptane, 1,7-diaziridinooctane, and 1,7-diaziridino-3-ethyloctane.

5. A process of claim 4 wherein the diamine is selected from: ethylene diamine, 1,6-diaminohexane, 1,12-diaminododecane, 2-methyl-1,5-diaminopentane, 1,4-bis(aminomethyl)cyclohexane, 1,3-diaminopentane, diethylenetriamine, 1,4-bis(3-aminopropyl)piperazine, 1,4-cyclohexanediamine, 5-amino-1-aminomethyl-1,3,3-trimethylcyclohexane, 1,3-propanediamine, 1,4-butanediamine, 1,5-pentanediamine, 1,7-heptanediamine, 1,8-diaminooctane, 1,9-diaminononane, 1,10-diaminodecane, 1,11-diaminoundecane, 2-hydroxy-1,3-propanediamine, and 4,4'-methylenebis(cyclohexylamine).

6. A method of claim 5 wherein the bifunctional organic compound is selected from: 1,10-dibromodecane, 1,12-dibromododecane, 1,8-dibromooctane, 1,18-dibromooctadecane, 1,9-dibromononane, 1,7-dibromoheptane, 1,8-diiodooctane, 1,8-dibromo-3-ethyloctane, and 1,9-dibromodecane, 1,9-diepoxydecane, 1,11-diepoxydodecane, 1,7-diepoxyoctane, 1,17-diepoxyoctadecane, 1,8-diepoxynonane, 1,6-diepoxyheptane, 1,7-diepoxyoctane, and 1,7-diepoxy-3-ethyloctane.

7. A process of claim 1 wherein Z is a hydrocarbylene radical containing 2–20 carbon atoms.

8. A process of claim 7 wherein Z is saturated.

9. A process of claim 8 wherein Z is an n-alkylene group containing 2–14 carbon atoms.

10. A process of claim 9 wherein Y is an n-alkylene group containing 7–20 carbon atoms.

11. A process of claim 10 wherein Y contains 7–14 carbon atoms.

12. A process of claim 11 wherein Y contains 9–12 carbon atoms.

13. A process of claim 6 wherein at least about 40% of the ammonium nitrogen atoms in the polymeric ammonium salt are secondary ammonium nitrogen atoms.

14. A process of claim 13 wherein 15 to 25% of the ammonium nitrogen atoms in the polymeric ammonium salt are primary ammonium nitrogen atoms, 40–60% of the ammonium nitrogen atoms are secondary ammonium nitrogen atoms, 15–25% of the ammonium nitrogen atoms are tertiary ammonium nitrogen atoms, and less than 5% of the ammonium nitrogen atoms are quaternary ammonium nitrogen atoms.

15. A process of claim 1 wherein the polymeric ammonium salt has a swell factor in water of at least about 4.

16. A process of claim 14 wherein the polymeric ammonium salt has a swell factor in water of at least 5.

17. A process of claim 16 wherein the polymeric ammonium salt has a swell factor in water of at least 10.

18. A process of claim 1 wherein said ammonium nitrogen atoms in the polymeric ammonium salt are further substituted with a hydrocarbyl group Q containing 1–50 carbon atoms, said hydrocarbyl group optionally containing one or more hydroxyl, ether, amino, thioether, keto, silyl groups, or heterocyclic ring.

19. The process of claim 18 wherein said Q contains 1 to 30 carbon atoms.

20. A method for lowering blood plasma cholesterol levels in a mammal, comprising, orally administering a therapeutically effective amount of a crosslinked polymeric ammonium salt product of claim 1.

21. A method for sequestering bile acids, comprising, contacting, in an aqueous medium, a bile acid and a crosslinked polymeric ammonium salt of claim 1.

22. A process of claim 1 wherein Y is decamethylene and Z is hexamethylene.

23. A process of claim 1 wherein Y is decamethylene and Z is tetramethylene.

24. A process of claim 1 wherein Y is decamethylene and Z is 2-hydroxy-1,3-propylene.

25. A process of claim 1 wherein Y is octamethylene and decamethylene and Z is not present.

26. A process of claim 1 wherein Z is 2-hydroxy-1,3-propylene or 2,7-dihydroxy-octamethylene.

27. A process of claim 8 wherein Z is an n-alkylene group containing 2–10 carbon atoms, optionally substituted with 1–2 hydroxy group(s).

28. A process of claim 1 wherein Y is decamethylene, Z is hexamethylene, and the template is a cellulose polymer.

29. A process of claim 1 wherein Y is decamethylene, Z is hexamethylene, and the template is selected from: methylcellulose, hydroxypropylcellulose, or carboxymethylcellulose.

30. A polymeric ammonium salt product of the process of claim 1.

31. A polymeric ammonium salt product of the process of claim 3.

32. A polymeric ammonium salt product of the process of claim 22.

33. A polymeric ammonium salt product of the process of claim 29.

34. A polymeric ammonium salt product of the process of claim 1 having a counterion which is selected from: chloride, bromide, iodide, sulfate, phosphate, acetate, ascorbate, carbonate, bicarbonate, nicotinate, salicylate, tartrate or citrate.

35. A polymeric ammonium salt product of the process of claim 33 having a counterion which is chloride.

36. A pharmaceutical composition comprising a pharmaceutically acceptable carrier and a therapeutically effective cholesterol lowering amount of a crosslinked polymeric ammonium salt product of claim 1.

* * * * *

UNITED STATES PATENT AND TRADEMARK OFFICE
CERTIFICATE OF CORRECTION

PATENT NO. : 5,556,619
DATED : September 17, 1996
INVENTOR(S) : Susan Durkee, et. al.

It is certified that error appears in the above-indentified patent and that said Letters Patent is hereby corrected as shown below:

Title page, item [73], Assignee: should read--The DuPont Merck Pharmaceutical Company and E. I. du Pont de Nemours and Company--.

Signed and Sealed this

Third Day of June, 1997

Attest:

BRUCE LEHMAN

Attesting Officer

Commissioner of Patents and Trademarks